United States Patent [19]

Yankee

[11] 4,128,725

[45] Dec. 5, 1978

[54] 16-PHENOXY-11β-PGE-ANALOGS

[75] Inventor: Ernest W. Yankee, Kalamazoo, Mich.

[73] Assignee: The Upjohn Company, Kalamazoo, Mich.

[21] Appl. No.: 824,871

[22] Filed: Aug. 15, 1977

Related U.S. Application Data

[63] Continuation of Ser. No. 684,637, May 10, 1976, abandoned.

[51] Int. Cl.$^2$ ............................................ C07C 177/00
[52] U.S. Cl. ...................................... 560/53; 562/463; 562/465; 260/343.3 P; 260/346.22
[58] Field of Search ........... 560/53; 260/520 R, 520 B

[56] References Cited

FOREIGN PATENT DOCUMENTS 2534989  8/1975  Fed. Rep. of Germany ............. 560/53

*Primary Examiner*—Paul J. Killos
*Attorney, Agent, or Firm*—Robert A. Armitage

[57] ABSTRACT

This invention comprises certain ω-aryl-ω-polynor analogs of the prostaglandins in which configuration of the 11-hydroxyl is beta. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

15 Claims, No Drawings

16-PHENOXY-11β-PGE-ANALOGS

This is a continuation of application Ser. No. 684,637, filed May 10, 1976, now abandoned.

BACKGROUND OF THE INVENTION

This invention provides novel compositions of matter.

Particularly this invention provides novel ω-aryl-ω-polynor analogs of some of the known prostaglandins which differ from corresponding known prostaglandins in that these prostaglandin analogs have an 11-hydroxyl of the opposite stereochemical configuration to the prostaglandins.

The known prostaglandins include the PGE compounds, e.g. prostaglandin $E_1$ ($PGE_1$), prostaglandin $E_2$ ($PGE_2$), prostaglandin $E_3$ ($PGE_3$), and dihydroprostaglandin $E_1$ (dihydro-$PGE_1$).

The known prostaglandins include $PGF_\alpha$ compounds, e.g. prostaglandin $F_{1\alpha}$ ($PGF_{1\alpha}$), prostaglandin $F_{2\alpha}$ ($PGF_{2\alpha}$), prostaglandin $F_{3\alpha}$ ($PGF_{3\alpha}$), and dihydroprostaglandin $F_{1\alpha}$ (dihydro-$PGF_{1\alpha}$).

The known prostaglandins include $PGF_\beta$ compounds, e.g. prostaglandin $F_{1\beta}$ ($PGF_{1\beta}$), prostaglandin $F_{2\beta}$ ($PGF_{2\beta}$), prostaglandin $F_{3\beta}$ ($PGF_{3\beta}$), and dihydroprostaglandin $F_{1\beta}$ (dihydro-$PGF_{1\beta}$).

Each of the above mentioned known prostaglandins (PG's) is a derivative of prostanoic acid which has the following structure and carbon atom numbering:

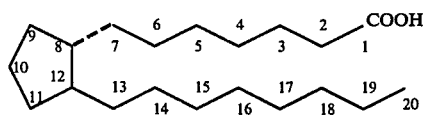

See, for example, Bergstrom et al., Pharmacol. Rev. 20, 1 (1968), and references cited therein. A systematic name for prostanoic acid is 7-[(2β-octyl)-cyclopent-1α-yl]heptanoic acid.

$PGE_1$ has the following structure:

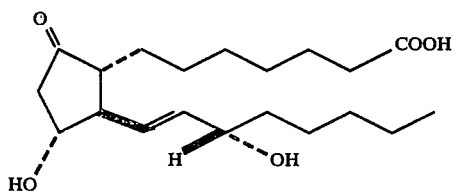

$PGE_2$ has the following structure:

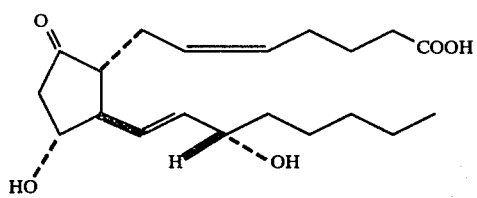

$PGE_3$ has the following structure:

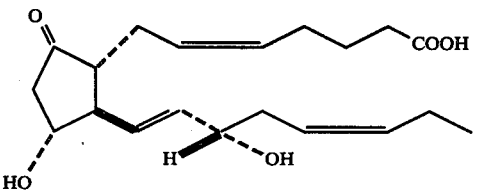

Dihydro-$PGE_1$ has the following structure:

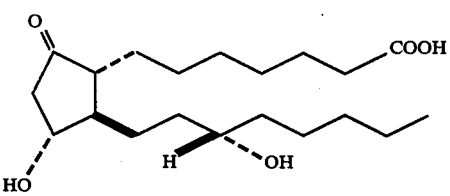

$PGF_{1\alpha}$ has the following structure:

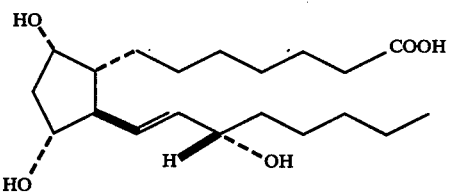

$PGF_{2\alpha}$ has the following structure:

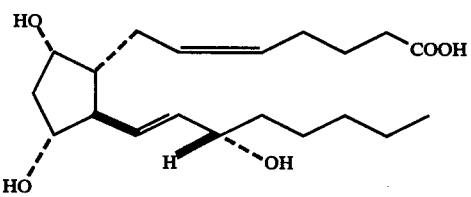

$PGF_{3\alpha}$ has the following structure:

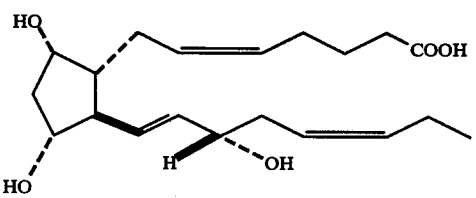

Dihydro-$PFG_{1\alpha}$ has the following structure:

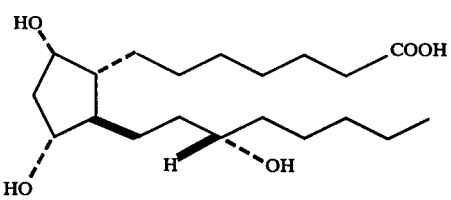

$PGF_{1\beta}$ has the following structure:

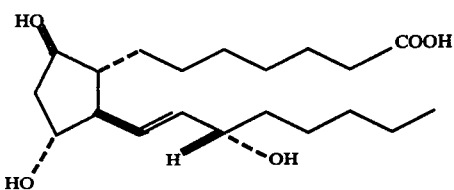

PGF$_{2\beta}$ has the following structure:

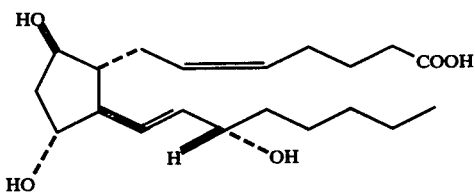

PGF$_{3\beta}$ has the following structure:

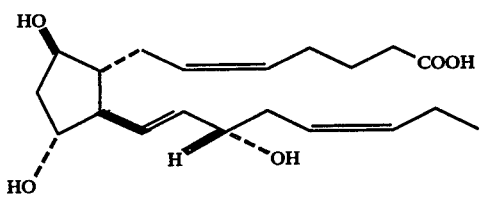

Dihydro-PGF$_{1\beta}$ has the following structure:

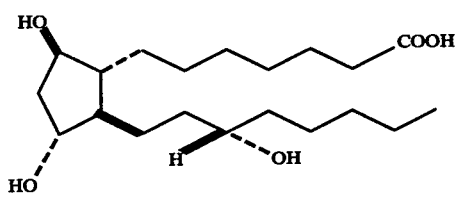

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring. The use of wavy lines (~) herein will represent attachment of substituents in either the alpha or beta configuration or attachment in a mixture of alpha and beta configurations.

The side-chain hydroxy at C-15 in the above formulas is in S configuration. See, Nature 212, 38 (1966) for discussion of the stereochemistry of the prostaglandins. Expressions such as C-13, C-14, C-15, and the like, refer to the carbon atom in the prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e. the dextrorotatory and levorotatory forms. As drawn, the above formulas each represent the particular optically active form of the prostaglandin as is obtained from mammalian tissues, for example, sheep vesicular glands, swine lung, or human seminal plasma, from carbonyl and/or double bond reduction of the prostaglandin so obtained. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of this formula is needed to represent correctly the corresponding racemic prostaglandin. For convenience hereinafter, use of the term, prostaglandin or "PG" will mean the optically active form of that prostaglandin thereby referred to with the same absolute configuration as PGE$_1$ obtained from mammalian tissues. When reference to the racemic form of one of those prostaglandins is intended, the word "racemic" or "dl" will precede the prostaglandin name.

The term "prostaglandin-type" (PG-type) product, as used herein, refers to any cyclopentane derivative which is useful for at least one of the same pharmacological purposes as the prostaglandins, as indicated herein.

The term prostaglandin-type intermediate, as used herein, refers to any cyclopentane derivative useful in preparing a prostaglandin-type product.

The formulas, as drawn herein, which depict a prostaglandin-type product or an intermediate useful in preparing a prostaglandin-type product, each represent the particular stereoisomer of the prostaglandin-type product which is of the same relative stereochemical configuration as a corresponding prostaglandin obtained from mammalian tissues, or the particular stereoisomer of the intermediate which is useful in preparing the above stereoisomer of the prostaglandin-type product.

The term "prostaglandin analog", as used herein, represents that stereoisomer of a prostaglandin-type product which is of the same relative stereochemical configuration as a corresponding prostaglandin obtained from mammalian tissues. In particular, where a formula is used to depict a prostaglandin-type compound herein, the term prostaglandin analog refers to the compound of that formula.

The various PG's named above, their esters, acylates and pharmacologically acceptable salts, are extremely potent in causing various biological responses. For that reason, these compounds are useful for pharmacological purposes. See, for example, Bergstrom et al., Pharmacol. Rev. 20, 1 (1968) and references cited therein.

For the PGE compounds these biological responses include:

(a) decreasing blood pressure (as measured, for example, in anesthetized, pentolinium-treated rats);

(b) stimulating smooth muscle (as shown by tests, for example, on guinea pig ileum, rabbit duodenum, or gerbil colon);

(c) effecting lipolytic activity (as shown by antagonism of epinephrine induced release of glycerol from isolated rat fat pads);

(d) inhibiting gastric secretion and reducing undesirable gastrointestinal effects from systematic administration of prostaglandin synthetase inhibitors;

(e) controlling spasm and facilitating breathing in asthmatic conditions;

(f) decongesting nasal passages;

(g) decreasing blood platelet adhesion (as shown by platelet to glass adhesiveness) and inhibiting blood platelet aggregation and thrombus formation induced by various physical stimuli (e.g., arterial injury) or chemical stimuli (e.g., ATP, ADP, serotinin, thrombin, and collagen);

(h) affecting the reproductive organs of mammals as labor inducers, abortifacients, cervical dilators, regulators of the estrus, and regulators of the menstrual cycle; and (j) accelerating growth of epidermal cells and keratin in animals.

For the $PGF_\alpha$ compounds these biological responses include:

(a) increasing blood pressure (as measured, for example, in anesthetized, pentolinium-treated rats);

(b) stimulating smooth muscle (as shown by tests on guinea pig ileum, rabbit duodenum, or gerbil colon);

(c) inhibiting gastric secretion and reducing undesirable gastrointestinal effects from systematic administration of prostaglandin synthetase inhibitors;

(d) controlling spasm and facilitating breathing in asthmatic conditions;

(e) decongesting nasal passages;

(f) decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and (g) affecting the reproductive organs of mammals as labor inducers, abortifacients, cervical dilators, regulators of the estrus, and regulators of the menstrual cycle.

For the $PGF_\beta$ compounds these biological responses include:

(a) decreasing blood pressure (as measured, for example, in anesthetized, pentolinium-created rats);

(b) stimulating smooth muscle (as shown by tests on guinea pig ileum, rabbit duodenum, or gerbil colon);

(c) inhibiting gastric secretion and reducing undesirable gastrointestinal effects from systematic administration of prostaglandin synthetase inhibitors;

(d) controlling spasm and facilitating breathing in asthmatic conditions;

(e) decongesting nasal passages;

(f) decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and (g) affecting the reproductive organis of mammals as labor inducers, abortifacients, cervical dilators, regulators of the estrus, and regulators of the menstrual cycle.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The prostaglandins so cited above as hypotensive agents are useful to reduce blood pressure in mammals, including man. For this purpose, the compounds are administered by intravenous infusion at the rate about 0.01 to about 50 $\mu$g. per kg. of body weight per minute or in single or multiple doses of about 25 to 500 $\mu$g. per kg. of body weight total per day.

The $PGF_\alpha$ compounds are useful in increasing blood pressure in mammals, including man. Accordingly, these compounds are useful in the treatment of shock (hemorrhagic shock, endotoxin shock, cardiogenic shock, surgical shock, or toxic shock). Shock is marked by pallor and clamminess of the skin, decreased blood pressure, feeble and rapid pulse, decreased respiration, restlessness, anxiety, and sometimes unconsciousness. Shock usually follows cases of injury and trauma. Expert and fast emergency measures are required to successfully manage such shock conditions. Accordingly, prostaglandins, combined with a pharmaceutical carrier which adapts the prostaglandin for intramuscular, intravenous, or subcutaneous use, are useful, especially in the early stages of shock where the need to increase blood pressure is a critical problem, for aiding and maintaining adequate blood flow, perfusing the vital organs, and exerting a pressor response by constricting veins and raising blood pressure to normal levels. Accordingly, these prostaglandins are useful in preventing irreversible shock which is characterized by a profound fall in blood pressure, dilation of veins, and venus blood pooling. In the treatment of shock, the prostaglandin is infused at a dose of 0.1–25 mcg./kg./min. The prostaglandin may advantageously be combined with known vasoconstrictors; such as phenoxy-benzamine, norepinephrine, and the like. Further, when used in the treatment of shock the prostaglandin is advantageously combined with steroids (such as, hydrocortisone or methylprednisolone), tranquilizers, and antibiotics (such as, lincomycin or clindamycin).

The compounds so cited above as extremely potent in causing stimulation of smooth muscle are also highly active in potentiating other known smooth muscle stimulators, for example, oxytocic agents, e.g., oxytocin, and the various ergot alkaloids including derivatives and analogs thereof. Therefore, these compounds for example, are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the prostaglandin is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperlum in the range 0.01 to 2 mg. per kg. of body weight per day, the exact dose depending on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The prostaglandins so cited above as useful in mammals, including man and certain useful animals, e.g., dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin and the antiinflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. Prostaglandins are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflamatory substance is being administered rectally, the prostaglandin is also administered rectally. Further, the prostaglandin can be conveniently administered orally, or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The prostaglandins so cited above as useful in the treatment of asthma, are useful, for example, as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories; parenterally; subcutaneously; or intramuscularly; with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The prostaglandins so cited above as useful in mammals, including man, as nasal decongestants are used for this purpose, in a dose range of about 10 μg. to about 10 mg. per ml. of a pharmacologically suitable liquid vehicle or as an aerosol spray, both for topical application.

The prostaglandins so cited above are useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts. to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, the compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The prostaglandins so cited above as useful in place of oxytocin to induce labor as used in pregnant female animals including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks postmature and natural labor has not started, or 12 to 60 hours after the membranes have ruptured and natural labor has not yet started. An alternative route of administration is oral.

These compounds are further useful for controlling the reproductive cycle in menstruating female mammals, including humans. By the term menstruating female mammals is meant animals which are mature enough to menstruate, but not so old that regular menstruation has ceased. For that purpose the prostaglandin is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin is administered locally or systemically.

The prostaglandin, for example, is administered orally or vaginally at doses of about 5 to 50 mg. per treatment of an adult female human, with from one to five treatments per 24 hour period. Alternatively the prostaglandin is administered intramuscularly or subcutaneously at doses of about 1 to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin is injected or applied in a feed at doses of 0.1-100 mg. per animal and may be combined with other agents such as steroids. Dosing schedules will depend on the species treated. For example, mares are given the prostaglandin 5 to 8 days after ovulation and return to estrus. Cattle, are treated at regular intervals over a 3 week period to advantageously bring all into estrus at the same time.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 μg. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

The compounds so cited above as promoters and accelerators of growth of epidermal cells and keratin are useful in animals, including humans, useful domestic animals, pet, zoological specimens, and laboratory animals for this purpose. For this reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separately or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 μg. per ml. of the prostaglandin. Especially for topical use, these prostaglandins are useful in combination with antibiotics, for example, gentamycin, neomycin, polymixin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone.

Various 11β-PG-type compounds are known in the art. See, for example, U.S. Pat. No. 3,862,984, which discloses 11β-PGF and PGE-type compounds and their corresponding 15-epimers. Further, see U.S. Pat. No. 3,839,430, which discloses various 13,14-didehydro-PGE$_1$, PGE$_1$, PGE$_2$, and PGE$_3$-type compounds of the 11β-hydroxyl configuration, and the corresponding 10-halo derivatives thereof. Additionally, see French Published application No. 2,239,241 (Derwent Farmdoc CPI 32908W/20) which discloses certain phenyl or phenoxy substituted 14-hydroxylated 11β-PG-type compounds. Additionally, see German Offenlegungsschrift No. 2,365,035 (Derwent Farmdoc CPI No. 50715V/28) which discloses certain trans-2,3-didehydro-PG$_1$-type compounds of both 11α- and 11β-hydroxy configuration. Additionally, Belgium Pat. No. 811,665 (Derwent Farmdoc CPI 57384V/30) describes various cycloalkyl containing prostaglandin analogs whose 11-position is substituted with an 11α-or 11β-hydroxyl. Further, Belgium Pat. No. 816,512 (Derwent Farmdoc CPI 00093W/01) describes certain 2-decarboxy-prostaglandin sulfonates substituted at the 11-position with an 11α- or 11β-hydroxyl. Likewise C-1 aldehydes corresponding to the above sulfonates are described in Belgium Pat. No. 824,196 (Derwent Farmdoc CPI 35976W/22). Additionally, German Offenlegungsschrift No. 2,505,519 describes certain ω-hydroxy methyl-prostaglandin analogs of an 11α- or 11β-hydroxyl configuration. Likewise German Offenlegungsschrift No. 2,515,770 (Derwent Farmdoc CP1 72798W/44) describes certain 15-cycloalkyl prostaglandin analogs of the 11α- or 11β-hydroxyl configuration. 11β-PGE$_2$ side chain homologs are described in French Published application No. 2,119,855 (Derwent Farmdoc CPI 76213T-B). Further, see U.S. Pat. No. 3,696,144 which describes 11β-13,14-dihydro-PGE$_1$ and 11β-8,12-didehydro-PGE$_1$. Further, see Netherlands Pat. No. 7,305,303 (Derwent Farmdoc CPI 66606U-B) which describes generically 11β-PGE$_1$ or PGE$_2$-type compounds and alkyl derivatives thereof. Further, see Netherlands Pat. No. 705,304 (Derwent Farmdoc CPI No. 66607U-B), which discloses 13,14-didehydro-PG-type compounds similar to those of the preceding reference. For additional 13,14-didehydro-11β-PG-type compound, see U.S. Pat. No. 3,392,496. Further, for 16-hydroxy-containing 8,12,13,14-tetradehydro-PGE-type compounds see U.S. Pat. No. 3,868,413 (Derwent Farmdoc CPI 17330W/10). Finally, see German Offenlegungsschrift No. 2,515,115 (Derwent Farmdoc CPI 71120W/43) which discloses certain 15-alkyl PGE$_1$ compounds with an 11β-hydroxyl configuration.

SUMMARY OF THE INVENTION

This invention provides novel prostaglandin analogs, esters of these analogs, and pharmacologically acceptable salts of these analogs.

This invention further provides lower alkanoates of these analogs.

The present invention comprises:
a prostaglandin analog of the formula

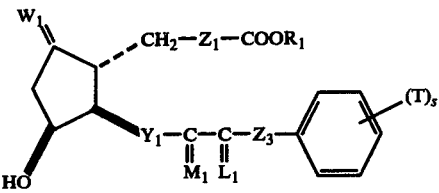

wherein $L_1$ is

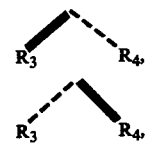

or a mixture of

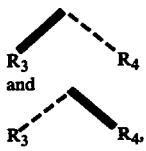

wherein $R_3$ and $R_4$ are hydrogen, methyl, or fluoro, being the same or different, with the proviso that one of $R_3$ and $R_4$ is fluoro only when the other is hydrogen of fluoro;
wherein $M_1$ is

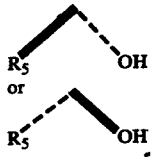

wherein $R_5$ is hydrogen or methyl;
wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $Z_3$ is oxa only when $R_3$ and $R_4$ are hydrogen or methyl, being the same or different;
wherein $W_1$ is

wherein $Y_1$ is trans-CH=CH— or —CH$_2$CH$_2$—;
wherein $Z_1$ is
(1) cis-CH=CH—CH$_2$—(CH$_2$)$_g$—CH$_2$—,
(2) cis-CH=CH—CH$_2$—(CH$_2$)$_g$—CF$_2$—,
(3) cis-CH$_2$—CH=CH—(CH$_2$)$_g$—CH$_2$—,
(4) —(CH$_2$)$_3$—(CH$_2$)$_g$—CH$_2$—; or
(5) —(CH$_2$)$_3$—(CH$_2$)$_g$—CF$_2$—
wherein g is 1, 2, or 3;
wherein $Z_3$ is oxa or methylene; and wherein R₁ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive or a pharmacologically acceptable cation.

Within the scope of the novel prostaglandin analogs of this invention, there are represented above:

(a) 11β-PGE-type compounds when the cyclopentane moiety is:

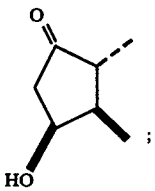

(b) 11β-PGF$_\alpha$-type compounds when the cyclopentane moiety is:

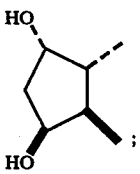

and (c) 11β-PGF$_\beta$-type compounds when the cyclopentane moiety is:

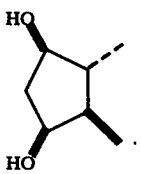

Those prostaglandin analogs herein wherein $Z_1$ is cis-CH=CH—CH$_2$—(CH$_2$)$_g$—CH$_2$— or cis-CH=CH—CH$_2$—(CH$_2$)$_g$—CF$_2$— are named as "PG$_2$" compounds. The latter compounds are further characterized as "2,2-difluoro" PG-type compounds. when g is 2 or 3, the prostaglandin analogs so described are "2a-homo" or "2a,2b-dihomo" compounds, since in this event the carboxy terminated side chain contains 8 or 9 carbon atoms, respectively, in place of the 7 carbon atoms contained in PGE$_1$. These additional carbon atoms are considered as though they were inserted between the C-2 and C-3 positions. Accordingly, these additional carbon atoms are referred to as C-2a and C-2b, counting from the C-2 to the C-3 position.

Further when $Z_1$ is —(CH$_2$)$_3$—(CH$_2$)$_g$—CH$_2$— or —(CH$_2$)$_3$—(CH$_2$)$_g$—CF$_2$, wherein g is as defined above, the compounds so described are "PG$_1$" or "2,2-difluoro-PG$_1$" compounds. When g is 2 or 3, the "2a-homo" and "2a,2b-dihomo" compounds are described as in discussed in the preceding paragraph.

When $Z_1$ is —CH$_2$—O—CH$_2$(CH$_2$)$_g$—CH$_2$— the compounds so described are named as "5-oxa-PG$_1$" compounds. When g is 2 or 3, the compounds so described are "2a-homo" or "2a,2b-dihomo" compounds, respectively, as discussed above.

When $Z_1$ is cis-CH$_2$—CH=CH—(CH$_2$)$_g$—CH$_2$—, wherein g is as defined above, the compounds so described are named "cis-4,5-didehydro-PG$_1$" compounds. When g is 2 or 3, the compounds so described are further characterized as "2a-homo" or "2a,2b-dihomo" compounds, respectively, as discussed above.

The novel prostaglandin analogs of this invention which contain a —CH$_2$CH$_2$— moiety at the C-13 to C-14 position, and are accordingly, referred to as "13,14-dihydro" compounds.

When $Z_3$ is methylene the compounds so described are named as "17-phenyl-18,19,20-trinor" compounds, when s is 0. When S is 1, 2, or 3, the corresponding compounds are named as "17-(substituted phenyl)-18,19,20-trinor" compounds.

When $Z_3$ is oxa and neither R$_3$ nor R$_4$ is methyl, the compounds so described are named as "16-phenoxy-17,18,19,20-tetranor" compounds, when s is zero. When s is 1, 2, or 3, the corresponding compounds are named as "16-(substituted phenoxy)-17,18,19,20-tetranor" compounds. When one and only one of R$_3$ and R$_4$ is methyl or both R$_3$ and R$_4$ are methyl, then the corresponding compounds wherein R$_7$ is as defined in this paragraph are named as "16-phenoxy or 16-(substituted phenoxy)-18,19,20-trinor" compounds or "16-methyl-16-phenoxy- or 16-(substituted phenoxy)-18,19,20-trinor" compounds, respectively.

When at least one of R$_3$ and R$_4$ is not hydrogen then (except for the 16-phenoxy compounds discussed above) there are described the "16-methyl" (one and only one of R$_3$ and R$_4$ is methyl), "16,16-dimethyl" (R$_3$ and R$_4$ are both methyl), "16-fluoro" (one and only one of R$_3$ and R$_4$ is fluoro), "16,16-difluoro" (R$_3$ and R$_4$ are both fluoro) compounds. For those compounds wherein R$_3$ and R$_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16S)".

When R$_5$ is methyl, the compounds so described are named as "15-methyl" compounds.

There is further provided by this invention both epimeric configurations of the hydroxy at C-15. As discussed herein, PGE$_1$, as obtained from mammalian tissues, has the "S" configuration at C-15. Further, as drawn herein PGE$_1$, as obtained from mammalian tissues, has the 15-hydroxy moiety in the "alpha" configuration.

For PGE$_1$ as obtained from mammalian tissues, the S configuration at C-15 represents the α-hydroxy configuration, using the convention by which the side chains of the novel prostaglandin analogs of this invention are drawn herein, as indicated above. Further, (15R)-PGE$_1$, by the convention used for drawing the prostaglandins herein, has the 15-hydroxy substituent in the beta configuration. Thus, the novel prostaglandin analogs of this invention wherein the 15-hydroxy moiety has the same absolute configuration as (15R)-PGE$_1$ at C-15 will be named "15-epi" compounds. When the designation "15-epi" is absent, those compounds wherein the configuration of the 15-hydroxy is the same as the absolute configuration of PGE$_1$ are represented, i.e., the 15α-hydroxy configuration.

Accordingly, as indicated by the preceding paragraphs, the novel PG analogs disclosed herein are named according to the system described in Nelson, N. A., J. Med. Chem. 17, 911 (1974).

Examples of alkyl of 1 to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of 1 to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

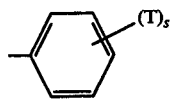

wherein T is alkyl of 1 to 3 carbon atoms, inclusive, fluoro, chloro, trifluoromethyl, or alkoxy of 1 to 3 carbon atoms, inclusive; and s is 0, 1, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-)chloro-2-fluorophenyl, o-, m-, or p-trifluoromethylphenyl, (o-, m-, or p-)methoxyphenyl, (o-, m-, or p-)ethoxyphenyl, (4- and 5-)chloro-2-methoxyphenyl, and 2,4-dichloro(5- or 6-)methylphenyl.

The novel prostaglandin analogs of this invention correspond to the prostaglandins described above, in that the novel prostaglandin analogs exhibit prostaglandin-like activity.

Specifically the PGE-type compounds of this invention correspond to the PGE compounds described above, in that these novel PGE-type compounds are useful for each of the above-described purposes for which the PGE compounds are used, and are used in the same manner as the PGE compounds, as described above.

The PGF$_\alpha$-type compounds of this invention correspond to the PGF$_\alpha$ compounds described above, in that these novel PGF$_\alpha$-type compounds are useful for each of the above-described purposes for which the PGF$_\alpha$ compounds are used, and are used in the same manner as the PGF$_\alpha$ compounds, as described above.

The PGF$_\beta$-type compounds of this invention correspond to the PGF$_\beta$ compounds described above, in that these novel PGF$_\beta$-type compounds are useful for each of the above-described purposes for which the PGF$_\beta$ compounds are used, and are used in the same manner as the PGF$_\beta$ compounds, as described above.

The prostaglandins described above, are all potent in causing multiple biological responses even at low doses. Moreover, for many applications, these prostaglandins have an inconveniently short duration of biological activity. In striking contrast, the novel prostaglandin analogs of this invention are substantially more selective with regard to potency in causing prostaglandin-like biological responses, and have a substantially longer duration of biological activity. Accordingly, each of these novel prostaglandin analogs is surprisingly and unexpectedly more useful than one of the corresponding prostaglandins described above for at least one of the pharmacological purposes indicated above for the latter, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Another advantage of the novel prostaglandin analogs of this invention, especially the preferred PG analogs defined hereinbelow, compared with the corresponding prostaglandins, is that these novel PG analogs are administered effectively orally, sublingually, intravaginally, buccally, or rectally in those cases wherein the corresponding prostaglandin is effective only by the intravenous, intramuscular, or subcutaneous injection or infusion methods of administration indicated above as uses of these prostaglandins. These alternate routes of administration are advantageous because they facilitate maintaining uniform levels of these compounds in the body with fewer, shorter, or smaller doses, and make possible self-administration by the patient.

Accordingly, the novel prostaglandin analogs of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the novel compounds of this invention be hydrogen or a pharmacologically acceptable cation. For subcutaneous of intramusclar injection, sterile solutions or suspensions of the acid, salt, or ester form in aqueous or non aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet of silicone rubber capsule or other object containing or impregnated with the substance is used.

The novel PG analogs of this invention are used for the purposes described above in the free acid form, in ester form, in pharmacologically acceptable salt form. When the ester form is used, the ester is any of those within the above definition of $R_1$. However, it is preferred that the ester by alkyl of 1 to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylgycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

The novel PG analogs of this invention are used for the purposes described above in free hydroxy form or also in the form wherein the hydroxy moieties are transformed to lower alkanoate moieties such as acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

To obtain the optimum combination of biological response specificity, potency, and duration of activity, certain compounds within the scope of this invention are preferred.

It is preferred that the carboxy-terminated side chain contain either 7 or 9 carbon atoms, especially preferred that it contains 7, i.e., the natural chian length of the prostaglandins. It is preferred that s be 0 or 1 and T be chloro, fluoro, or trifluoromethyl.

For those compounds wherein at least one of $R_3$ and $R_4$ is methyl or fluoro, it is preferred that $R_5$ be hydrogen. For those compounds wherein $R_5$ is methyl, it is preferred that $R_3$ and $R_4$ both be hydrogen.

It is further preferred that the 15-hydroxy or 15-methoxy not be of the 15-epi configuration, i.e., that the hydroxy be in the alpha configuration when the formulas of the novel PG analogs are as drawn herein.

Especially preferred are those compounds which satisfy two or more of the above preferences. Further, the above preferences are expressly intended to describe the preferred compounds within the scope of any generic formula of novel prostaglandin analogs disclosed herein. Thus, for example the above preferences describe preferred compounds within the scope of each formula of a prostaglandin analog provided in the Tables hereinafter.

In another aspect of the interpretation of the preferences herein, the various prostaglandin cyclopentane, ring structures as empolyed herein are each representative of a particular "parent structure" which is useful in naming and categorizing the novel prostaglandin analogs disclosed herein. Further, where a formula depicts a genus of PG analogs disclosed herein evidencing a single cyclopentane ring structure, then each corresponding genus of PG analogs evidencing one of the remaining cyclopentane ring structures cited herein for novel prostaglandin analogs is intended to represent an equally preferred genus of compounds. Thus, for example, for each genus of $PGF_\alpha$-type products depicted by a formula herein, the corresponding genera of $PGF_\beta$- and PGE-type products are equally preferred embodiments of the invention as the genera of $PGF_\alpha$-type products.

Finally where subgeneric groupings of PG analogs of any cyclopentane ring structure are described herein, then the corresponding subgeneric groupings of PG analogs of each of the remaining cyclopentane ring structures are intended to represent equally preferred embodiments of the present invention.

With respect to Chart A, a method is provided whereby the novel prostaglandin analogs of this invention are prepared.

With respect to the symbols employed in Chart A, T, s, $Z_1$, $Z_3$, g, $L_1$, $R_1$, $M_1$, $Y_1$, and $W_1$ are as defined above. $R_2$ is hydrogen or fluoro, $R_9$ is an acyl separating group and n is 1 or 2. $M_5$ is a mixture of

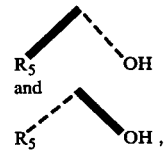

wherein $R_5$ is as defined above. $M_{15}$ is a mixture of

and

wherein $R_9$ and $R_5$ are as defined above. $M_{16}$ is

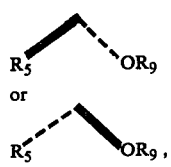

wherein $R_5$ and $R_9$ are defined above. $M_7$ is

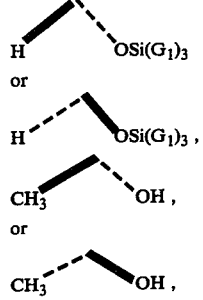

wherein —Si($G_1$)$_3$ is a silyl group as is defined hereinafter.

$G_1$ is alkyl of 1 to 4 carbon atoms, cycloalkyl of 3 to 10 carbon atoms, inclusive, aralkyl of 7 to 12 carbon atoms, phenyl, or phenyl substituted with 1 or 2 fluoro, chloro, or alkyl of 1 to 4 carbon atoms, with the proviso that in the —Si—($G_1$)$_3$ moiety the various $G_1$'s are the same or different. $R_{38}$ is hydrogen or —O—Si—($G_1$)$_3$, wherein $G_1$ is as defined above.

CHART A

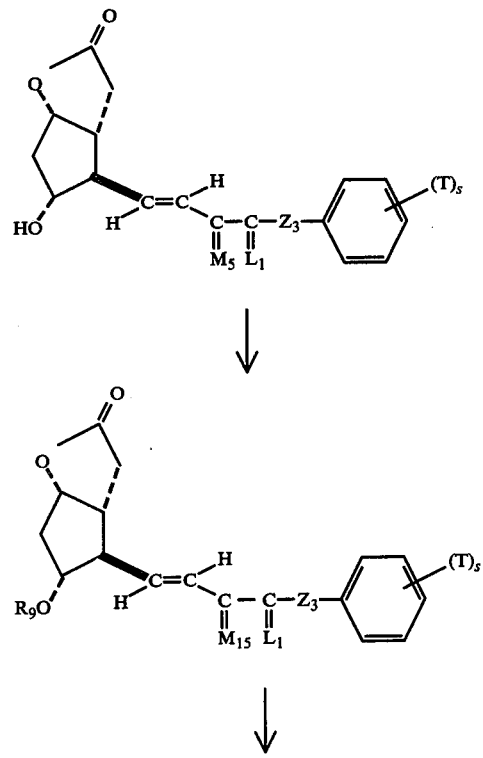

-continued
CHART A

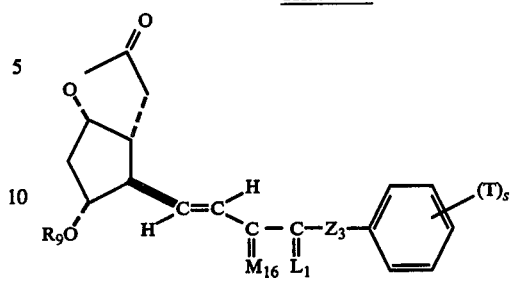
XXIII

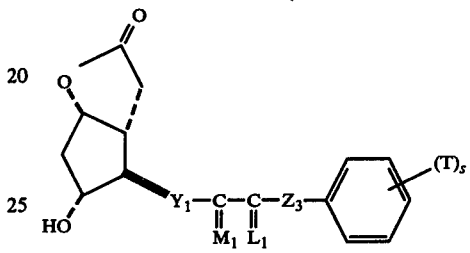
XXIV

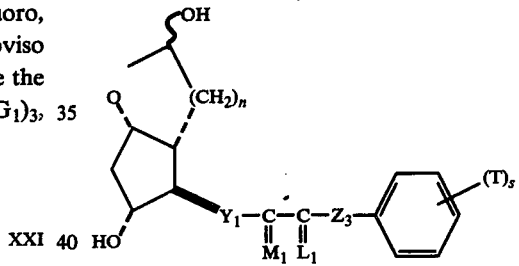
XXV

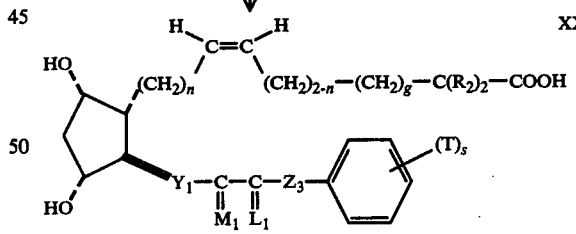
XXVI

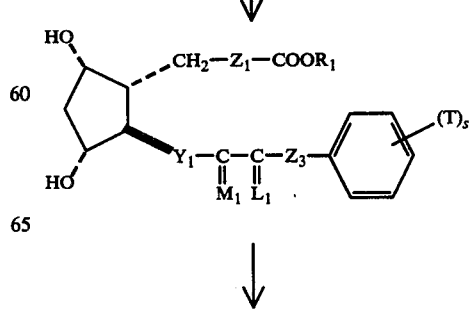
XXVII

-continued
CHART A

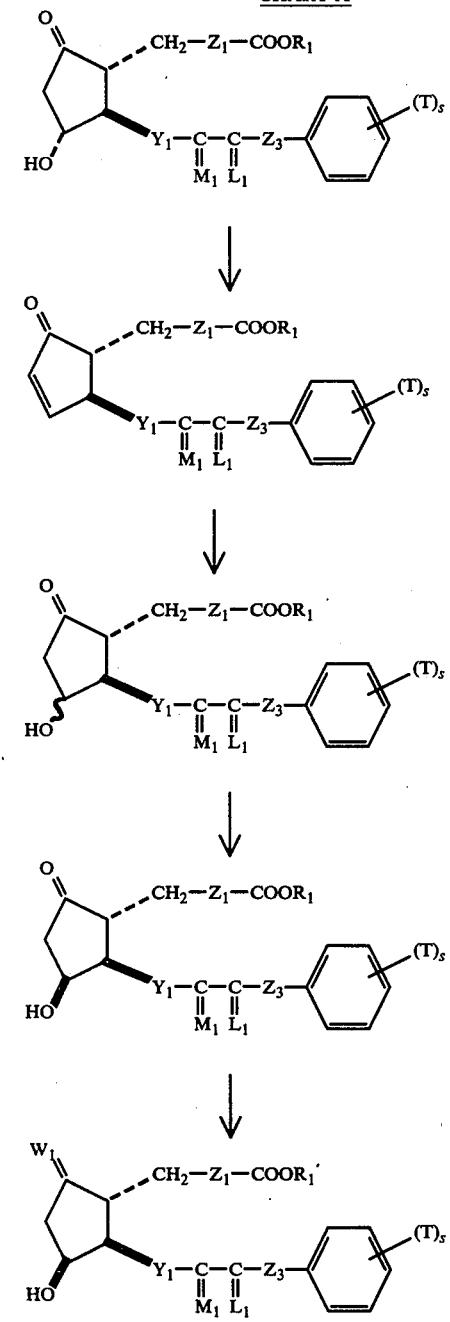

$R_9$ is, as indicated above, an acyl separating group. Acyl separating groups according to $R_9$, include:
 (a) Benzoyl;
 (b) Benzoyl substituted with one to 5, inclusive, alkyl of one to 4 carbon atoms, inclusive, phenylalkyl of 7 to 12 carbon atoms, inclusive, or nitro, with the proviso that not more than 2 substituents are other than alkyl, and that the total number of carbon atoms in the substituents does not exceed 10 carbon atoms, with the further proviso that the substituents are the same or different;
 (c) Benzoyl substituted with alkoxycarbonyl of 2 to 5 carbon atoms, inclusive;
 (d) Naphthoyl; and
 (e) Naphthoyl substituted with one to 9, inclusive, alkyl of 1 to 4 carbon atoms, inclusive, phenylalkyl of 7 to 10 carbon atoms, inclusive, or nitro, with the proviso that not more than two substituents on either of the fused aromatic rings are other than alkyl and that the total number of carbon atoms in the substituents on either of the fused aromatic rings does not exceed 10 carbon atoms, with the further proviso that the various substituents are the same or different.

In preparing these acyl derivatives of a hydroxy-containing compound herein, methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g., sulfuric acid, zinc chloride, or phosphoryl chloride; or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxy-containing compound in the presence of a hydrogen chloride scavenger, e.g. a tertiary amine such as pyridine, triethylamine or the like. The reaction is carried out under a variety of conditions, using procedures generally known in the art. Generally mild conditions are employed: 20°-60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_9OH$), anhydrides ($(R_9)_2O$), or acyl chlorides ($R_9Cl$): benzoyl; substituted benzoyl, e.g., 2-, 3-, or 4-)-methylbenzoyl, (2-, 3-, or 4-)-ethyl benzoyl, (2-, 3-, or 4-)-isopropylbenzoyl, (2-, 3-, or 4-)-tert-butylbenzoyl, 2,4-dimethylbenzoyl, 3,5-dimethylbenzoyl, 2-isopropyltolyl, 2,4,6-trimethylbenzoyl, pentamethylbenzoyl, alphaphenyl (2-, 3-, or 4-)-toluyl, (2-, 3-, or 4-)-phenethylbenzoyl, (2-, 3-, or 4-)-nitrobenzoyl, (2,4-, 2,5-, or 2,3-)-dinitrobenzoyl, 2,3-dimethyl-2-nitrobenzoyl, 4,5-dimethyl-2-nitrobenzoyl, 2-nitro-6-phenethylbenzoyl, 3-nitro-2-phenylethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)-methyl-1-naphthoyl, (2- or 4-) ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g. tert-butyl on both of the ring carbon atoms adjacent to the carbonyl attaching cite.

The acyl separating groups, according to $R_9$, are removed by deacylation. Alkali metal carbonates are employed effectively at ambient temperature for this purpose. For example, potassium carbonate in methanol at about 25° C. is advantageously employed.

Chart A provides a method whereby the novel formula XXXIII prostaglandin analogs of the present invention are prepared. For those formula XXX compounds which are readily available, the novel formula XXXIII compounds are prepared therefrom employing the reaction sequence XXX to XXXIII. When these formula XXX compounds are not readily available, they are prepared by the reaction sequence XXI to XXX.

The formula XXI compounds are known in the art, or readily prepared by methods known in the art. For example, the $\alpha,\beta$-unsaturated ketone corresponding to formula XXI is transformed to the formula XXI compound by sodium borohydride reduction or by a Grignard reaction, as is known in the art.

The reaction sequence XXI to XXIV is then employed as a means by which the epimeric mixture of formula XXI is separated. Accordingly, the formula XXI compound is transformed to the formula XXII compound by acylation. Methods for the introduction of acyl separating groups, described above, are employed. Thereafter, the formula XXII compound is transformed to the formula XXIII compound by conventional methods known to separate the diastereomeric prostaglandins. For example, silica gel chromatography or high pressure liquid chromatography are employed.

Thereafter, the formula XXIII compound is transformed to the formula XXIV compound by deacylation, employing methods described above; followed by optionally catalytically hydrogenating the deacylated compound so formed when $Y_1$ is $-CH_2CH_2-$.

The transformation of the formula XXIV compound to the formula XXV compound wherein $n$ is 2, is achieved by a multistep chemical synthesis. The general method by which the formula XXV compound is thusly prepared is generally described in German Offenlegungschriften Nos. 2,317,019 and 2,320,552. Accordingly, the formula XXIV compound is reduced to a corresponding lactol, employing methods known in the art for the transformation of bicyclic prostaglandin lactone intermediates to corresponding bicyclic prostaglandin lactol intermediates (e.g. the use of diisobutylaluminum hydride at $-78°$ C.). Thereafter this lactol is condensed with, for example, an alkoxymethylene-triphenylphosphorane. See, for reference, Levine, Journal of the American Chemical Society 80, 6150 (1958). The resulting enol intermediate thus formed is hydrolyzed to the formula XXV lactol, for example, under acidic conditions with perchloric acid or acetic acid. Tetrahydrofuran is used for a diluent for this purpose and reaction temperatures of from 10° to 100° C. are employed.

Alternatively, the hydrolysis of the enol ether of the preceding paragraph to the corresponding lactol is accomplished in the presence of methanol and under mild acidic conditions pH 2 buffer so that a $\delta$ lactol methyl ether ($\sim OCH_3$ rather than $\sim OH$) is formed and isolated. This $\delta$ lactol methyl ether is then hydrolyzed under slightly stronger acidic conditions (pH 1 aqueous buffer), to the formula XXV compound.

The formula XXV compound wherein $n$ is 1 is prepared from the formula XXIV compound by reduction with diisobutyl-aluminum hydride, as described above.

Thereafter, the formula XXV compound is transformed to the formula XXVI compound by a Wittig alkylation. Procedures generally known in the art are employed. Wittig reagents such as the triphenylphosphonium salt of the formula

$$Br^{\ominus}(C_6H_5)_3P^{\oplus}(CH_2)_{\overline{n-2}}(CH_2)_g-C(R_2)_2-COOH$$

wherein $n$, $g$, and $R_2$ are as defined above, are employed.

Thereafter the formula XXVII compound is prepared from the formula XXVI compound wherein $n$ is 1 by catalytic hydrogenation, followed in any event by an optional esterification of the formula XXVI free acid to an $R_1$ ester. Methods known and described below are employed. Thereafter the formula XXVII compound is transformed to the formula XXVIII compound by first selectively silylating all secondary hydroxy hydrogens except at C-9, thereafter oxidizing the C-9 hydroxy to a 9-oxo compound, and finally hydrolyzing the silyl blocking groups.

In employing this selective silylation, silyl groups of the formula $-S_i(G_1)_3$, wherein G is alkyl of 1 to 4 carbon atoms, inclusive, alkyl of 7 to 12 carbon atoms, inclusive, phenyl, phenyl substituted with 1 or 2 chloro, fluoro, or alkyl of 1 to 4 carbon atoms, inclusive, with the proviso that the various G's of the $-S_i(G_1)_3$ moiety are the same or different, are employed. Reagents for preparing the various silyl groups are known in the art and the procedures for selective silylation are likewise known in the art. See for reference U.S. Pat. No. 3,822,303, German Offenlegungsschrift No. 2,259,195 (Derwent Farmdoc CPl 36457U-B), and Netherlands Pat. No. 7,214,142 (Derwent Farmdoc CPl 26221U-B). See the immediately preceding references for examples of useful silyl groups.

The selectively silylated compound is then oxidized and the silyl groups hydrolyzed, thereby preparing the formula XXVIII compound. This oxidation proceeds by methods known in the art for the transformation of PGF-type compounds to corresponding PGE-type compounds. Accordingly, the Collins reagent is employed by methods known in the art. Finally, the silyl groups are hydrolyzed by methods known in the art. For example, the use of dilute aqueous acetic acid in combination with the silylated compound in a sufficient quantity of water miscible solvent so as to achieve a homogenous reaction mixture as employed. This hydrolysis is ordinarily complete within 2 to 12 hr. at 25° C. and is preferably carried out in an atmosphere of an inert gas such as nitrogen or argon.

The formula XXVIII compound is then transformed to the corresponding formula XXX PGA-type compound in two steps. First, any secondary hydroxyls of the formula XXVIII compound are transformed to corresponding alkanoates, preferably acetates, by methods known in the art. Thus, the corresponding acid anhydride, e.g. acetic anhydride, is employed for this purpose. Thereupon, the highly unstable 11-acylate rapidly dehydrates to the corresponding PGA-type compound either on standing at room temperature or, if more rapid dehydration is desired, by contacting the acylated compound with silica gel. Thereafter, the deacylation at C-15 proceeds by methods known in the art for hydrolyzing these ester linkages. When concomitant hydrolysis of the C-2 carboxy ester is effected, the ester is conveniently restored employing esterification techniques hereinbelow described. Thus, the formula XXX PGA-type compound is prepared. As discussed above, however, many of these formula XXX PGA-type compounds are known in the art.

These formula XXX compounds are then transformed to the formula XXXIII 11β-PGE-type compounds employing methods known in the art. Thus, the formula XXX compound is transformed to the corresponding 9,10-epoxide, and said epoxide is reduced to the corresponding (11RS)-PGE-type compound of formula XXXI, and this formula XXXI compound is separated, preparing the formula XXXII 11β-PGE-type compound. See, U.S. Pat. No. 3,862,984, for a detailed description of the transformation of the formula XXX compound to the formula XXXII compound. See, particularly, Chart A therein.

Finally, the formula XXXII compound is transformed to the various formula XXXIII compounds by a cyclopentane ring carbonyl reduction of the formula XXXII compound to the corresponding 9α- or 9β-hydroxy compounds of formula XXXIII. Methods known in the art for the transformation of PGE-type compounds to corresponding $PGF_\alpha$- or $PGF_\beta$-type compounds are employed. Thus, Chart A provides the method whereby each of the novel prostaglandin analogs of the present invention are prepared.

Optically active PG-type products are obtained from optically active intermediates, according to the process steps of the above chart. Likewise optically active PG-type compounds are obtained from corresponding optically active PG-type compounds following the procedures in the above chart.

In all of the above described reactions, the products are separated by conventional means from starting material and impurities. For example, by use of silica gel chromatography monitored by thin layer chromatography the products of the various steps of the above charts are separated from the corresponding starting materials and impurities.

As discussed above, the processes herein described lead variously to acids ($R_1$ is hydrogen) or to esters.

When the alkyl ester has been obtained and an acid is desired, saponification procedures, as known in the art for PGF-type compounds are employed.

For alkyl esters of PGE-type compounds enzymatic processes for transformation of esters to their acid forms may be used by methods known in the art when saponification procedures would cause dehydration of the prostaglandin analog. See for reference E. G. Daniels, Process For Producing An Esterase, U.S. Pat. No. 3,761,356.

When an acid has been prepared and an alkyl, cycloalkyl, or aralkyl ester is desired, esterification is advantageously accomplished by interaction of the acid in the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about 1 to about 10 minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389-394 (1954).

An alternative method for alkyl, cycloalkyl or aralkyl esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing phenyl or substituted phenyl esters within the scope of the invention from corresponding aromatic alcohols and the free acid PG-type compounds, differing as to yield and purity of product.

Thus by one method, the PG-type compound is converted to a tertiary amine salt, reacted with povaloyl halide to give the mixed acid anhydride and then reacted with the aromatic alcohol. Alternatively, instead of pivaloyl halide, an alkyl or arylsulfonyl halide is used, such as p-toluenesulfonyl chloride. See for example Belgian Pat. Nos. 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231-236, John Wiley and Sons, Inc., New York, (1967). The PG-type compound is contacted with one to ten molar equivalents of the aromatic alcohol in the presence of 2-10 molar equivalents of dicyclohexylcarbodiimide in pyridine as a solvent.

One preferred novel process for the preparation of these esters, however, comprises the steps:

(a) forming a mixed anhydride with the PG-type compound and isobutylchloroformate in the presence of a tertiary amine and (b) reacting the anhydride with an appropriate aromatic alcohol.

The mixed anhydride described above is formed readily at temperatures in the range $-40°$ to $+60°$ C., preferably at $-10°$ to $+10°$ C. so that the rate is reasonably fast and yet side reactions are minimized. The isobutylchloroformate reagent is preferably used in excess, for example 1.2 molar equivalents up to 4.0 per mole of the PG-type compound. The reaction is preferably done in a solvent and for this purpose acetone is preferred, although other relatively nonpolar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The aromatic alcohol is preferably used in equivalent amounts or in substantial stoichiometric excess to insure that all of the mixed anhydride is converted to ester. Excess aromatic alcohol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they are effectively used, 2-methylpyridine and quinoline result in a slow reaction. A highly hindered amine such as 2,6-dimethyllutidine is, for example, not useful because of the slowness of the reaction.

The reaction with the anhydride proceeds smoothly at room temperature (about 20° to 30° C.) and can be followed in the conventional manner with thin layer chromatography (TLC).

The reaction mixture is worked up to yield the ester following methods known in the art, and the product is purified, for example by silica gel chromatography.

Solid esters are converted to a free-flowing crystalline form on crystallization from a variety of solvent, including ethyl acetate, tetrahydrofuran, methanol, and acetone, by cooling or evaporating a saturated solution of the ester in the solvent or by adding a miscible non-solvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

The acids or esters of this invention prepared by the processes of this invention are transformed to lower alkanoates by interaction of a free hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, or hexanoic anhydride gives the corresponding carboxyacylate.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent.

An inert organic diluent, (e.g., dioxane) can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24 hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography or crystallization.

DESCRIPTION OF THE PREFERRED EMBODIMENTS

The invention can be more fully understood by the following examples and preparations.

All temperatures are indegrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, and T-60 spectrophotometer on deuterochloroform solutions with tetramethylsilane as an internal standard (downfield).

Mass spectra are recorded on an CEC model 21-110B Double Focusing High Resolution Mass Spectrometer on an LKB Model 9000 Gas-Chromatography-Mass Spectrometer. Trimethylsilyl derivatives are used, except where otherwise indicated.

The collection of chromatographic eluate fractions starts when the eluant front reaches the bottom of the column.

"Brine", herein, refers to an aqueous saturated sodium chloride solution.

The A-IX solvent system used in thin layer chromatography is made up from ethyl acetate-acetic acid-cyclohexane-water (90:20:50:100) as modified from M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

DDQ refers to 2,3-dichloro-5,6-dicyano-1,4-benzoquinone.

THF refers to tetrahydrofuran.

Specific rotations, [α], are determined for solutions of a compound in the specified solvent at ambient temperature with a Perkin-Elmer Model 141 Automatic Polarimeter.

PREPARATION 1

15-Methyl-16-phenoxy-17,18,19,20-tetranor-13,14-dihydro-PGA$_2$, methyl ester, (Formula XXX: $Z_1$ is cis—CH=CH—(CH$_2$)$_3$—, $M_1$ is

$Z_3$ is oxa, $R_3$ and $R_4$ of the $L_1$ moiety are hydrogen, $Y_1$ is —CH$_2$CH$_2$—, and $R_1$ is methyl).

Refer to Chart A.

A.

A solution of the formula XXI compound, 3α,5α-dihydroxy-2β-[(3RS)-3-methyl-3-hydroxy-4-phenoxy-trans-1-butenyl]-1α-cyclopentaneacetic acid γ lactone (26.5 g.), in 1.06 l. of dry pyridine under a nitrogen atmosphere at 0° C. with stirring is combined with 530 ml. of benzoylchloride. The resulting solution is then stirred for 15 min. at ambient temperature, then at 70° C. for 5 hr. The resulting mixture is then cooled to ambient temperature and then to 0° C. To this cooled solution is added 90 ml. of water dropwise. The resulting mixture is then stirred at 0° C. for an additional 30 min. then at ambient temperature for 24 hr. The resulting mixture is then equilibrated with 1 l. of ethyl acetate in 4 l. of aqueous sulfuric acid and ice (prepared from 370 ml. of concentrated sulfuric acid). The phases are separated and the aqueous phase extracted with ethyl acetate. The organic extracts are combined, washed with water, and thereafter washed with aqueous sodium bicarbonate.

The aqueous sodium bicarbonate wash is then extracted with ethyl acetate. The organic extracts are combined, washed with brine, dried over sodium sulfate, and evaporated to yield a dark viscous oil. (formula XXII).

B.

A column packed with 1800 g. of silica gel slurried in methylene chloride is used to chromatograph 24.2 g. of the reaction product of part A above. Eluting with 1 to 2 percent acetone in methylene chloride those fractions as shown by thin layer chromatography to contain pure (3R)- or (3S)- epimer are combined. (formula XXIII).

C.

A solution of sodium methoxide in methanol is prepared by dissolving 8.5 g. of sodium in 175 ml. of anhydrous methanol with stirring and cooling under a nitrogen atmosphere. This solution is then slowly added to a slurry of 12.8 g. of the (3R)-epimer of part B in 170 ml. of anhydrous methanol under nitrogen. The reaction is stirred at ambient temperature for 7 days and the reaction thereafter quenched by addition to a cold equilibrated mixture of 300 ml. of 2M sodium sulfate, ice, and 500 ml. of ethyl acetate. Upon equilibration the aqueous phase is separated and extracted with ethyl acetate. The organic extracts are then combined, washed with water, saturated Na$_2$HPO$_4$, saturated sodium bicarbonate and brine. Drying with sodium sulfate and evaporation yields crude product. The crude product is then subjected to silica gel chromatography on a column packed with 25 percent ethyl acetate in Skellysolve B, eluting with 50 percent ethyl acetate in Skellysolve B. Combining fractions shown to contain pure product by thin layer chromatography, there is obtained a formula XXIV compound wherein $Y_1$ is trans-CH=CH—.

D.

A mixture of 4.0 g. of the (3R)-epimeric product of part C above, 800 mg. of a 5 percent palladium-on-charcoal catalyst, and 400 ml. of ethyl acetate is stirred at ambient temperature under one atmosphere of hydrogen for 1 hour. Hydrogen uptake proceeds rapidly and the reaction is stopped when thin layer chromatography shows the reaction to be complete. The resulting mixture is filtered through Celite and washed with ethyl acetate. The filtrate is then evaporated to an oil. Characteristic NMR absorptions are observed at 0.7–3.3, 1.15, 3.8–4.3, and 4.7–5.1 δ. (formula XXIV wherein $Y_1$ is —CH$_2$CH$_2$—).

E.

To a stirred solution of the (3R)-epimeric product of part D above (3.7 g.) in 135 ml. of tetrahydrofuran at −78° C. under a nitrogen atmosphere is added 110 ml. of 10 percent diisobutylaluminum hydride in toluene. When thin layer chromatography of an aliquot quenched in diethyl ether and sodium bisulfate shows the reaction to be complete, the reaction is then quenched by addition of 135 ml. of saturated ammonium chloride. The resulting mixture is then stirred and allowed to warm to ambient temperature. The mixture is then shaken and filtered through Celite, washing well with ethyl acetate in water. The filtrate is equilibrated and the aqueous phase separated and extracted well with ethyl acetate. The organic extracts are then combined, washed with brine, dried over sodium sulfate, and evaporated to yield a formula XXV compound wherein n is one.

F.

A slurry of 4.4 g. of a 57 percent dispersion of sodium hydride in mineral oil and 110 ml. of dimethyl sulfoxide under nitrogen is stirred at 75° C. for 1.5 hr. and thereafter cooled to ambient temperature. To this solution is then added 21.5 g. of 4-carboxybutyltriphenylphosphonium bromide in 10 ml. of dimethylsulfoxide. The resulting mixture is then stirred at ambient temperature for 1 hr. Thereafter there is added to this mixture 3.7 g. of the (3R)-epimeric reaction product of part E above in 35 ml. of dimethylsulfoxide. The resulting solution is then stirred at ambient temperature for 16 hr. until the reaction is shown to be complete by thin layer chromatography. The reaction is then quenched by addition of the reaction mixture to an equilibrated mixture of sodium bisulfate, ice, and diethyl ether. After equilibration the aqueous phase is extracted with diethyl ether and the organic extracts combined, washed with sodium hydroxide and thereafter washed with water. The sodium hydroxide solution is then cooled by addition of ice and equilibrated with diethyl ether. The iced mixture is then acidified by addition of sodium bisulfate. After equilibration the aqueous phase is extracted well with diethyl ether and the organic extracts then combined, washed with water, brine and dried with sodium sulfate. The resulting mixture is then evaporated to an oil which is then chromatographed to yield pure 15-methyl-16-phenoxy-17,18,19,20-tetranor-13,14-dihydro-PGF$_{2\alpha}$ (formula XXVI).

Following the procedure of parts A–F, but using in place of the lactone diol starting material of formula XXI the corresponding formula XXI lactone diols wherein s is one, and T is chloro, fluoro, or trifluoromethyl, or R$_3$ and R$_4$ are methyl, or both, there are corresponding 13,14-dihydro-15-methyl-PGF$_{2\alpha}$-type compounds.

Further, following the procedure of Preparation 1, but using in place of 4-carboxybutyltriphenylphosphonium bromide either 5-carboxypentyltriphenylphosphonium bromide or 6-carboxyhexyltriphenylphosphonium bromide there is prepared respectively the 2a-homo- or 2a,2b-dihomo- or 15-methyl-13,14-dihydro-PGF$_{2\alpha}$-type compounds.

Further, following the procedure of Preparation 1, but replacing the benzoyl chloride, employed in part A, with various substituted benzoyl chlorides, there is prepared the same product.

G.

The (15R)- product of Part F is dissolved in a mixture of diethyl ether and methanol (1:1) and thereafter treated with a stoichiometric excess of diazomethane in diethyl ether. Evaporation of solvent yields crude product which when chromatographed on 450 g. of silica gel yields the corresponding methyl ester.

H.

To a stirred solution of 1.0 g. of 13,14-dihydro-15-methyl-16-phenoxy-17,18,19,20-tetranor-PGF$_{2\alpha}$, methyl ester (part G) in 40 ml. of acetone under nitrogen at −45° C. is added 4.0 g of trimethylsilyldiethylamine. Resulting solution is then stirred at −45° C. for 3 hr. When the reaction is shown to be complete by thin layer chromatography the solution is then diluted with 160 ml. of diethyl ether (cooled to −78° C.). The resulting solution is then added to 200 ml. of partially saturated sodium bicarbonate. After equilibration, the aqueous phase is extracted with diethyl ether. The ethereal extracts are combined, washed with saturated sodium bicarbonate and brine, and thereafter dried over sodium sulfate. The resulting mixture is then evaporated to yield the 11-trimethysilyl derivative of the starting material.

I.

To a stirred solution of 2.0 g. of anhydrous chromium trioxide in 100 ml. of methylene chloride at ambient temperature under nitrogen is added 3.25 g. of dry pyridine. The resulting mixture is then stirred at ambient temperature for 2 hr. and thereafter cooled to 0° C. To this mixture is added 1.1 g. of 13,14-dihydro-15-methyl-16-phenoxy-17,18,19,20-tetranor-PGF$_{2\alpha}$, 11-trimethylsilyl ether, methyl ester, the reaction product of part H above, in 20 ml. of methylene chloride. The resulting mixture is stirred at room temperature for 10 min. and thereafter filtered through 10 cm of silica gel, washing well with ethyl acetate. The filtrate is then evaporated to yield the PGE-type compound corresponding to the starting material of this part.

J.

The crude product from part I above is dissolved in 60 ml. of methanol. To this solution at room temperature is added with stirring 30 ml. of water and 3 ml. of acetic acid. The resulting solution is then stirred for 30 min. at room temperature. This mixture is then added to 100 ml. of a 2M solution of sodium bisulfate and 100 ml. of diethyl ether. After equilibration the aqueous phase is extracted with diethyl ether. The ethereal extracts are then combined, washed with water, and brine, and thereafter dried with sodium sulfate. Upon evaporation 15-methyl-13,14-dihydro-16-phenoxy-17,18,19,20-tetranor-PGE$_2$, methyl ester is obtained (formula XXVIII).

K.

To a stirred solution of 100 mg. of 13,14-dihydro-15-methyl-16-phenoxy-17,18,19,20-tetranor-PGE$_2$, methyl ester (part J) in 3.3 ml. of dry pyridine at ambient temperature under nitrogen is added 1 ml. of acetic anhydride. After 2.5 hr. the reaction mixture is cooled to 0° C. and 3.3 ml. of methanol is added. The reaction mixture is then stirred for 5 min. at 0° C. and thereafter for 18 hr. at ambient temperature. The reaction is then quenched by addition to an equilibrated mixture of sodium bisulfate, ice and diethyl ether. The aqueous extract is then washed well with diethyl ether and the organic extracts are combined, washed with water, saturated sodium bicarbonate, and brine. The resulting mixture is thereafter dried over sodium sulfate and evaporated to give the crude 11-acetate of the starting material.

L.

The crude product from the preceding paragraph is then chromatographed on 8 gm. of silica gel packed in 100 percent ethyl acetate eluting with 50 percent ethyl acetate in hexane. Fractions shown to be pure by thin layer chromatography are then combined yielding the title formula XXX compound.

Following the procedure described in Preparation 1, but using in place of the 15-methyl- or 15-epi-15-methyl-13,14-dihydro-16-phenoxy-17,18,19,20-tetranor-PGF$_{2\alpha}$ starting material of part F therein the various other PGF$_{2\alpha}$-type compounds described following part F, there are obtained the corresponding products.

EXAMPLE 1

15-Methyl-13,14-dihydro-16-phenoxy-17,18,19,20-tetranor-11β-PGE$_2$, methyl ester and corresponding PGF$_{2\alpha}$ and PGF$_{2\beta}$ compounds (Formula XXXIII: Z$_1$ is cis-CH=CH—(CH$_2$)$_3$—, R$_1$ is methyl, Y$_1$ is —CH$_2$CH$_2$—, M$_1$ is

$R_3$ and $R_4$ of the $L_1$ moiety are both hydrogen, $Z_3$ is oxa, and s is 0).

Refer to Chart A.

A.

Following the procedure of Example 11 of U.S. Pat. No. 3,862,984, the reaction product of Preparation 1 is epoxidized to the corresponding 10,11-epoxide; reduced to the corresponding (11RS)-PGE-type compound; and chromatographically separated on silica gel, yielding the 11$\beta$-PGE-type title product.

B.

Following the procedure of Example 17 of U.S. Pat. No. 3,862,984, but employing the reaction product of part A of this example, there are obtained the 11$\beta$-PGF$_{2\alpha}$- and 11$\beta$-PGF$_{2\beta}$-type title products.

Following the procedure of Example 1, but employing each of the various PGA-type compounds of formula XXX, there are obtained each of the various 11$\beta$-PG-type products of the present invention.

Particularly and especially there are obtained those products described in the succeeding tables.

In interpreting these tables, each formula listed in the table represents a prostaglandin-type product whose complete name is given by combining the name provided in the respective legends below each formula with the prefix found in the "Name" column in the tabular section of the tables for each example therein.

Table A

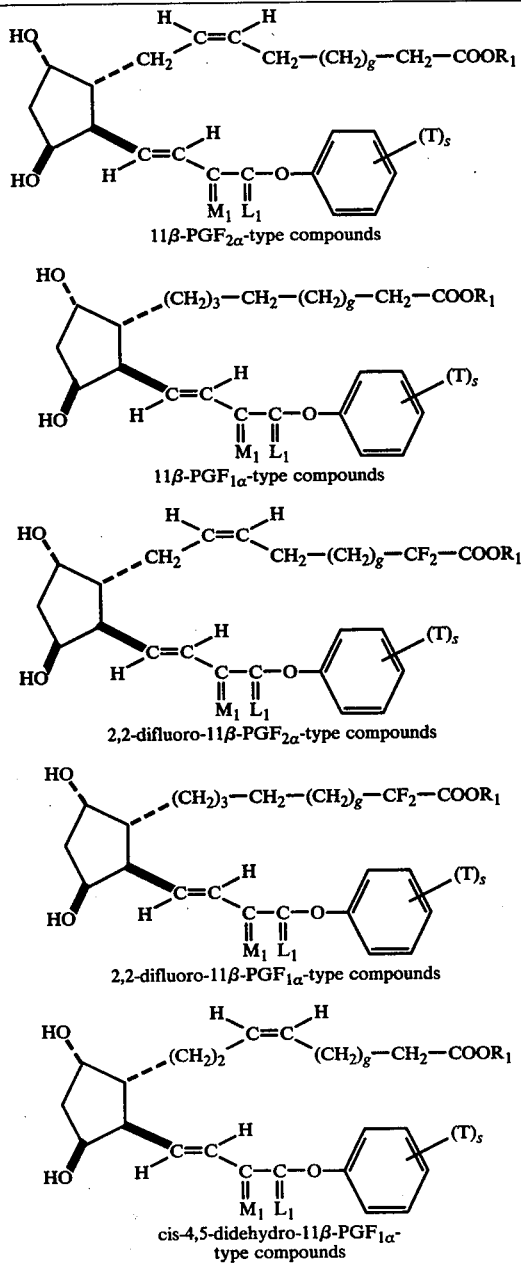

Table A-continued
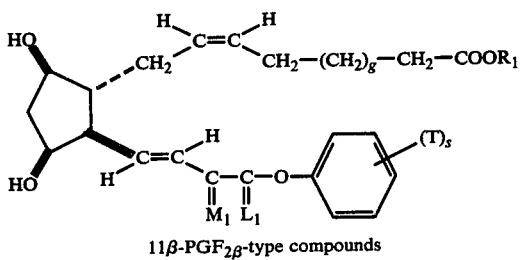
11β-PGF$_{2β}$-type compounds
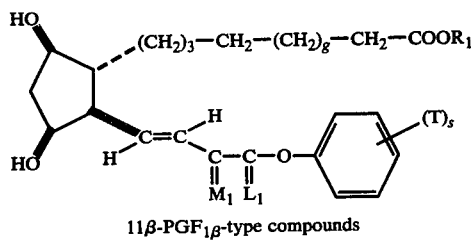
11β-PGF$_{1β}$-type compounds
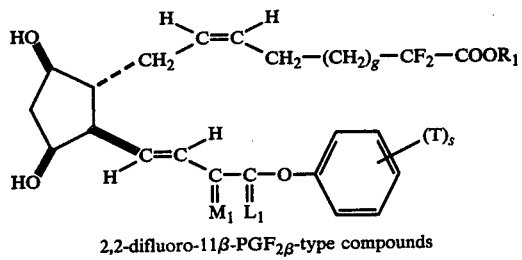
2,2-difluoro-11β-PGF$_{2β}$-type compounds
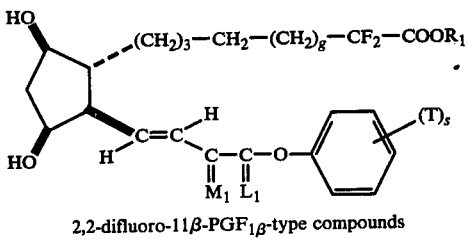
2,2-difluoro-11β-PGF$_{1β}$-type compounds
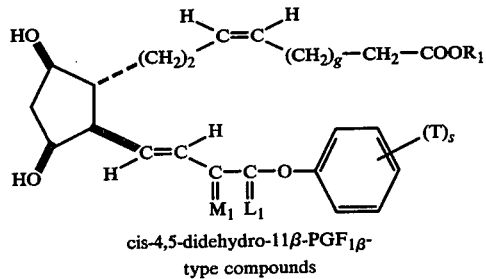
cis-4,5-didehydro-11β-PGF$_{1β}$-
type compounds
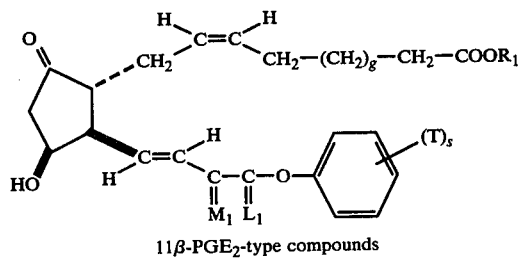
11β-PGE$_2$-type compounds Table A-continued
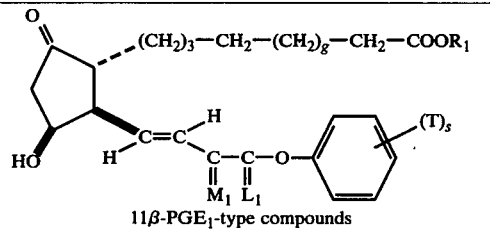
11β-PGE₁-type compounds
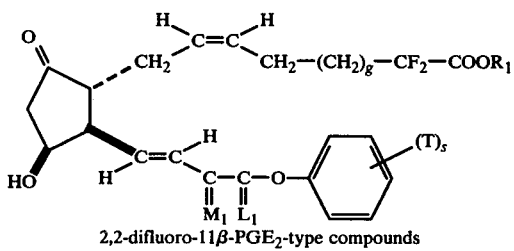
2,2-difluoro-11β-PGE₂-type compounds
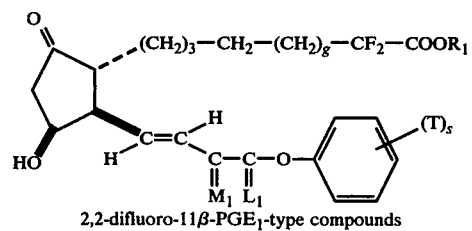
2,2-difluoro-11β-PGE₁-type compounds
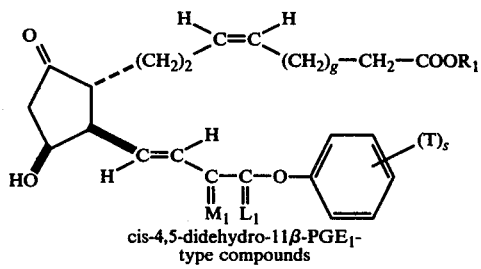
cis-4,5-didehydro-11β-PGE₁-type compounds
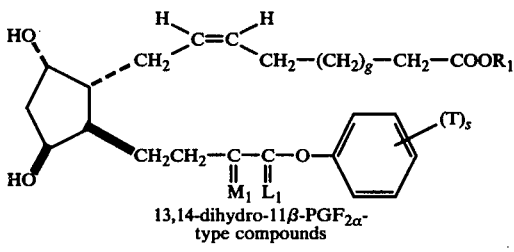
13,14-dihydro-11β-PGF₂α-type compounds
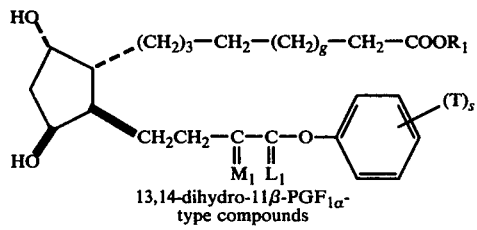
13,14-dihydro-11β-PGF₁α-type compounds
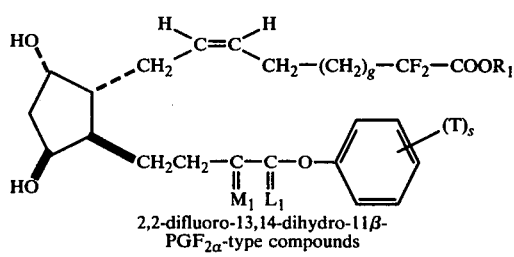
2,2-difluoro-13,14-dihydro-11β-PGF₂α-type compounds Table A-continued
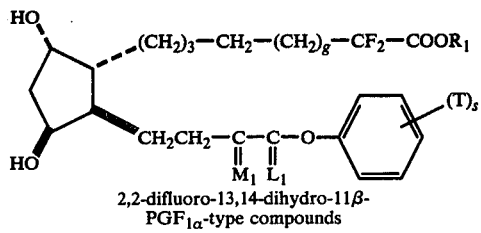
2,2-difluoro-13,14-dihydro-11β-PGF$_{1α}$-type compounds
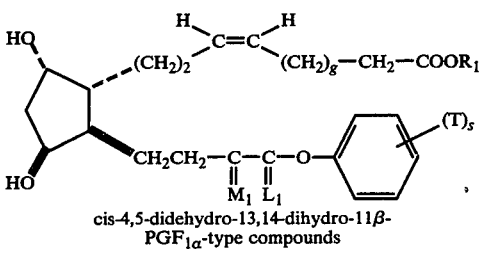
cis-4,5-didehydro-13,14-dihydro-11β-PGF$_{1α}$-type compounds
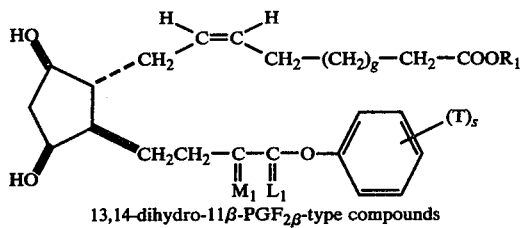
13,14-dihydro-11β-PGF$_{2β}$-type compounds
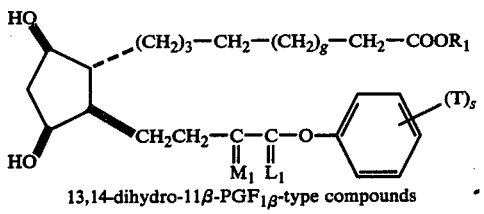
13,14-dihydro-11β-PGF$_{1β}$-type compounds
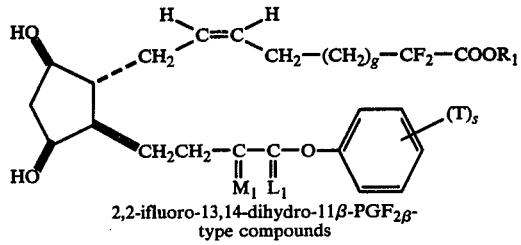
2,2-ifluoro-13,14-dihydro-11β-PGF$_{2β}$-type compounds
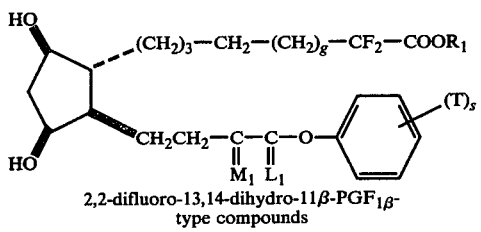
2,2-difluoro-13,14-dihydro-11β-PGF$_{1β}$-type compounds
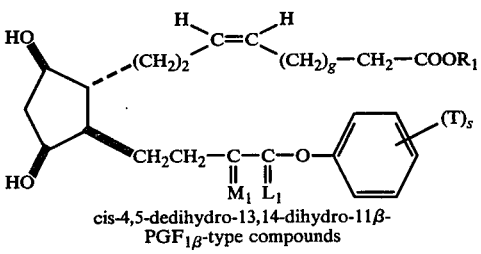
cis-4,5-dedihydro-13,14-dihydro-11β-PGF$_{1β}$-type compounds

Table A-continued

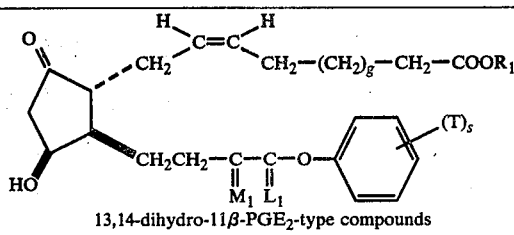
13,14-dihydro-11β-PGE$_2$-type compounds

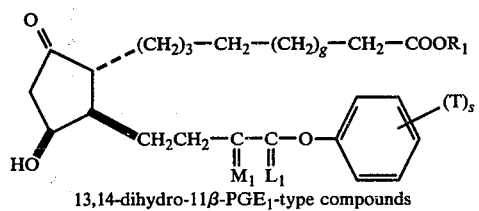
13,14-dihydro-11β-PGE$_1$-type compounds

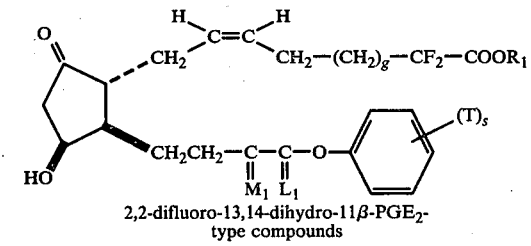
2,2-difluoro-13,14-dihydro-11β-PGE$_2$-type compounds

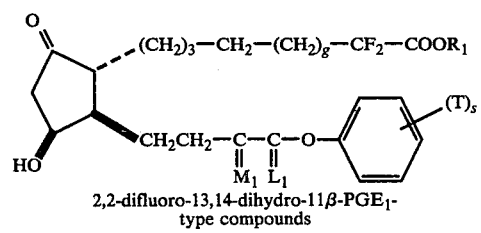
2,2-difluoro-13,14-dihydro-11β-PGE$_1$-type compounds

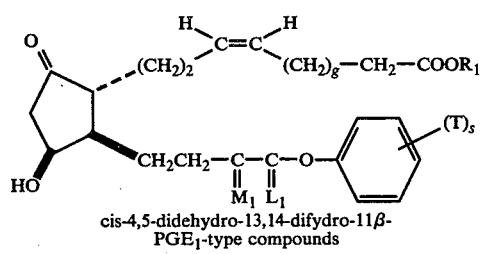
cis-4,5-didehydro-13,14-difydro-11β-PGE$_1$-type compounds

| Example | g | s | T | L$_1$ R$_3$ | R$_4$ | M$_1$ R$_5$ | ~OH | R$_1$ | Name |
|---|---|---|---|---|---|---|---|---|---|
| A-1 | 1 | 0 | | hydrogen | hydrogen | hydrogen | α | hydrogen | 16-phenoxy-17,18,19,20-tetranor |
| A-2 | 1 | 1 | p-fluoro | hydrogen | hydrogen | hydrogen | α | hydrogen | 16-(p-fluorophenoxy)-17,18,19,20-tetranor |
| A-3 | 1 | 1 | m-chloro | hydrogen | hydrogen | hydrogen | α | hydrogen | 16-(m-chlorophenoxy)-17,18,19,20-tetranor |
| A-4 | 1 | 1 | m-trifluoromethyl | hydrogen | hydrogen | hydrogen | α | hydrogen | 16-(m-trifluoromethylphenoxy)-17,18,19,20-tetranor |
| A-5 | 1 | 0 | | hydrogen | hydrogen | methyl | α | hydrogen | 15-methyl-16-phenoxy-17,18,19,20-tetranor |
| A-6 | 1 | 1 | p-fluoro | hydrogen | hydrogen | methyl | α | hydrogen | 15-methyl-16-(p-fluorophenoxy)-17,18,19,20-tetranor |
| A-7 | 1 | 1 | m-chloro | hydrogen | hydrogen | methyl | α | hydrogen | 15-methyl-16-(m-chlorophenoxy)-17,18,19,20-tetranor |
| A-8 | 1 | 1 | m-trifluoromethyl | hydrogen | hydrogen | methyl | α | hydrogen | 15-methyl-16-(m-trifluoromethylphenoxy)-17,18,19,20-tetranor |
| A-9 | 1 | 0 | | methyl | methyl | hydrogen | α | hydrogen | 16-methyl-16-phenoxy-18,19,20-trinor |
| A-10 | 1 | 1 | p-fluoro | methyl | methyl | hydrogen | α | hydrogen | 16-methyl-16-(p-fluorophenoxy)-18,19,20-trinor |
| A-11 | 1 | 1 | m-chloro | methyl | methyl | hydrogen | α | hydrogen | 16-methyl-16-(m-chlorophenoxy)-18,19,20-trinor |
| A-12 | 1 | 1 | m-trifluoromethyl | methyl | methyl | hydrogen | α | hydrogen | 16-methyl-16-(m-trifluoromethylphenoxy)-18,19,20-trinor |
| A-13 | 1 | 0 | | methyl | methyl | methyl | α | hydrogen | 15,16-dimethyl-16-phenoxy-18,19,20-trinor |

Table A-continued

| | | | | | | | | |
|---|---|---|---|---|---|---|---|---|
| A-14 | 1 | 1 | p-fluoro | methyl | methyl | methyl | α | hydrogen | 15,16-dimethyl-16-(p-fluorophenoxy)-18,19,20-trinor |
| A-15 | 1 | 1 | m-chloro | methyl | methyl | methyl | α | hydrogen | 15,16-dimethyl-16-(m-chlorophenoxy)-18,19,20-trinor |
| A-16 | 1 | 1 | m-trifluoromethyl | methyl | methyl | methyl | α | hydrogen | 15,16-dimethyl-16-(m-trifluoromethylphenoxy)-18,19,20-trinor |
| A-17 | 3 | 0 | | hydrogen | hydrogen | hydrogen | α | hydrogen | 2a,2b-dihomo-16-phenoxy-17,18,19,20-tetranor |
| A-18 | 3 | 1 | p-fluoro | hydrogen | hydrogen | hydrogen | α | hydrogen | 2a,2b-dihomo-16-(p-fluorophenoxy)-17,18,19,20-tetranor |
| A-19 | 3 | 1 | m-chloro | hydrogen | hydrogen | hydrogen | α | hydrogen | 2a,2b-dihomo-16-(m-chlorophenoxy)-17,18,19,20-tetranor |
| A-20 | 3 | 1 | m-trifluoromethyl | hydrogen | hydrogen | hydrogen | α | hydrogen | 2a,2b-dihomo-16-(m-trimethylphenoxy)-17,18,19,20-tetranor |
| A-21 | 3 | 1 | | hydrogen | hydrogen | methyl | α | hydrogen | 2a,2b-dihomo-15-methyl-16-phenoxy-17,18,19,20-tetranor |
| A-22 | 3 | 1 | p-fluoro | hydrogen | hydrogen | methyl | α | hydrogen | 2a,2b-dihomo-15-methyl-16-(p-fluorophenoxy)-17,18,19,20-tetranor |
| A-23 | 3 | 1 | m-chloro | hydrogen | hydrogen | methyl | α | hydrogen | 2a,2b-dihomo-15-methyl-16-(m-chlorophenoxy)-17,18,19,20-tetranor |
| A-24 | 3 | 1 | m-trofluoromethyl | hydrogen | hydrogen | methyl | α | hydrogen | 2a,2b-dihomo-15-methyl-16-(m-trifluoromethylphenoxy)-17,18,19,20-tetranor |
| A-32 | 1 | 1 | m-trifluoromethyl | fluoro | fluoro | methyl | α | hydrogen | 15-methyl-16,16-difluoro-17-(m-trifluoromethylphenoxy) |

Table B

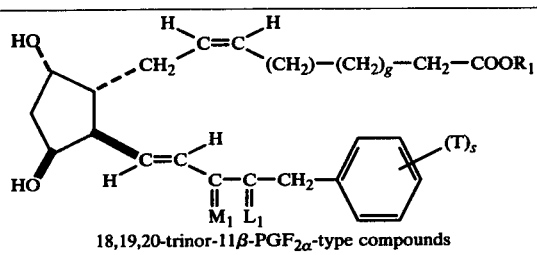

18,19,20-trinor-11β-PGF$_{2\alpha}$-type compounds

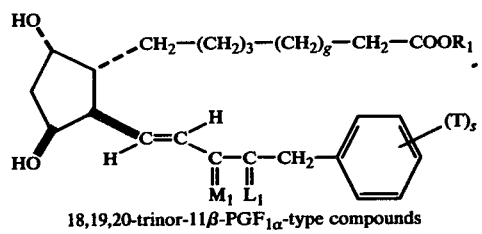

18,19,20-trinor-11β-PGF$_{1\alpha}$-type compounds

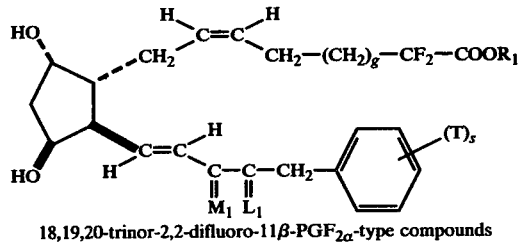

18,19,20-trinor-2,2-difluoro-11β-PGF$_{2\alpha}$-type compounds

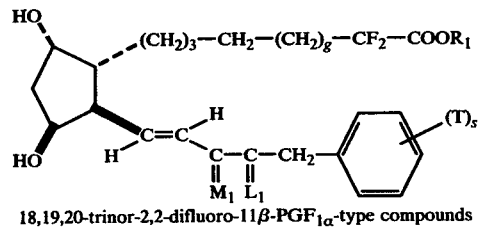

18,19,20-trinor-2,2-difluoro-11β-PGF$_{1\alpha}$-type compounds

Table B-continued
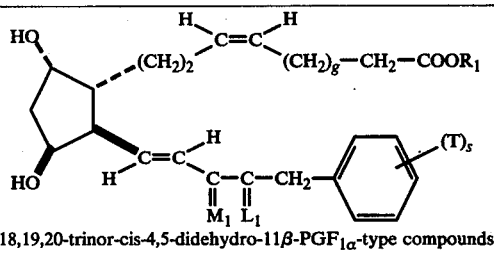
18,19,20-trinor-cis-4,5-didehydro-11β-PGF$_{1α}$-type compounds
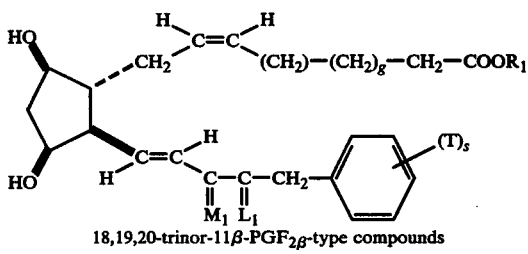
18,19,20-trinor-11β-PGF$_{2β}$-type compounds
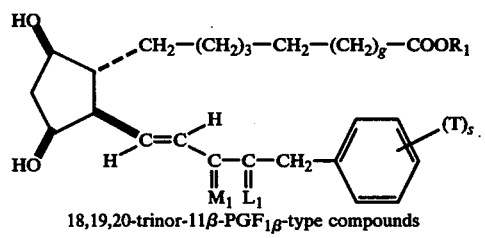
18,19,20-trinor-11β-PGF$_{1β}$-type compounds
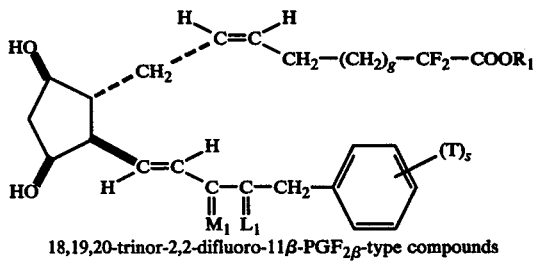
18,19,20-trinor-2,2-difluoro-11β-PGF$_{2β}$-type compounds
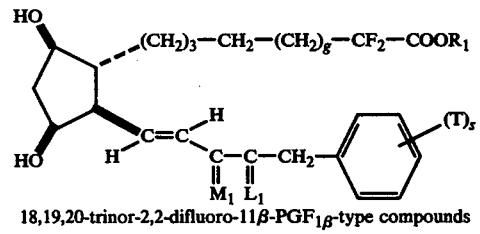
18,19,20-trinor-2,2-difluoro-11β-PGF$_{1β}$-type compounds
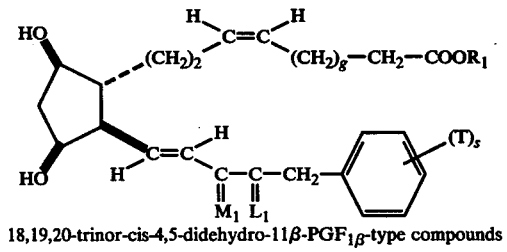
18,19,20-trinor-cis-4,5-didehydro-11β-PGF$_{1β}$-type compounds
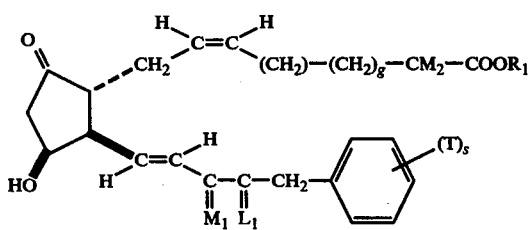

Table B-continued
18,19,20-trinor-11β-PGE₂-type compounds
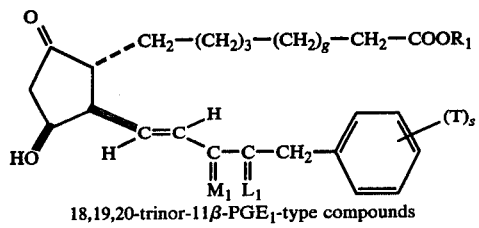
18,19,20-trinor-11β-PGE₁-type compounds
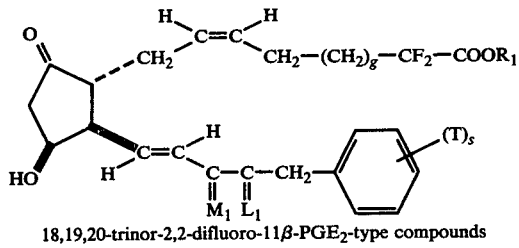
18,19,20-trinor-2,2-difluoro-11β-PGE₂-type compounds
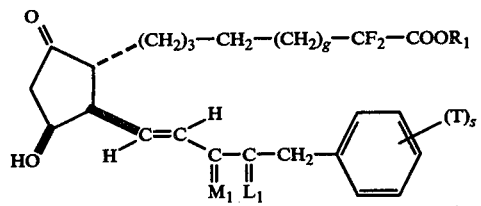
18,19,20-trinor-2,2-difluoro-11β-PGE₁-type compounds
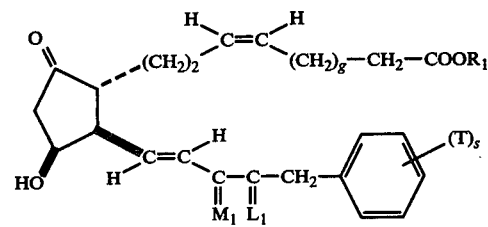
18,19,20-trinor-cis-4,5-didehydro-11β-PGE₁-type compounds
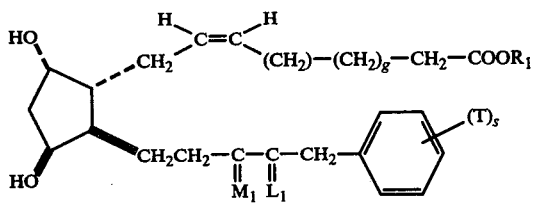
18,19,20-trinor-13,14-dihydro-11β-PGF₂α-type compounds
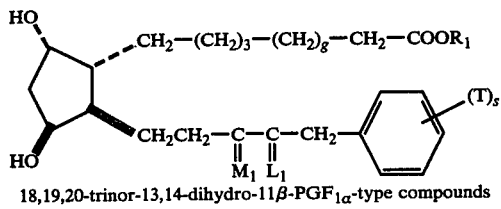
18,19,20-trinor-13,14-dihydro-11β-PGF₁α-type compounds
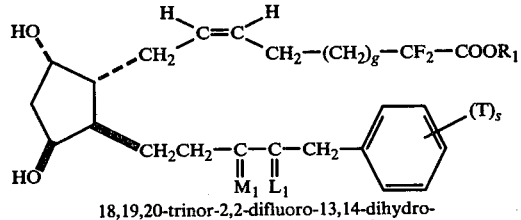
18,19,20-trinor-2,2-difluoro-13,14-dihydro-11β-PGF₂α-type compounds Table B-continued

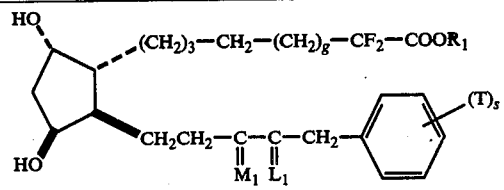
18,19,20-trinor-2,2-fluoro-13,14-dihydro-
11β-PGF$_{1\alpha}$-type compounds

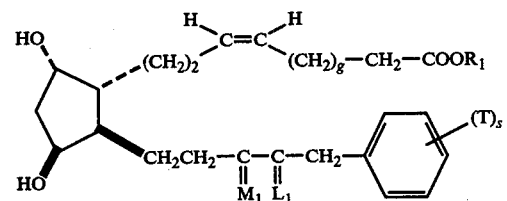
18,19,20-trinor-cis-4,5-didehydro-13,14-dihydro-
11β-PGF$_{1\alpha}$-type compounds

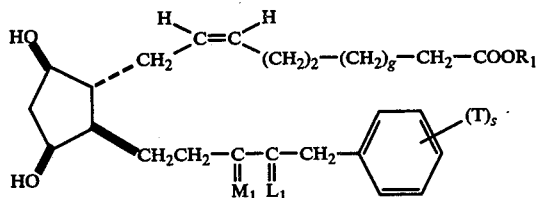
18,19,20-trinor-13,14-dihydro-11β-PGF$_{2\beta}$-type compounds

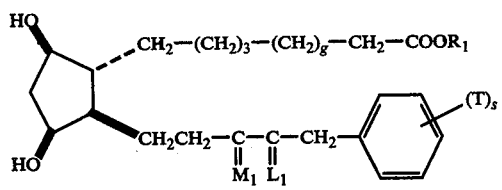
18,19,20-trinor-13,14-dihydro-11β-PGF$_{1\beta}$-type compounds

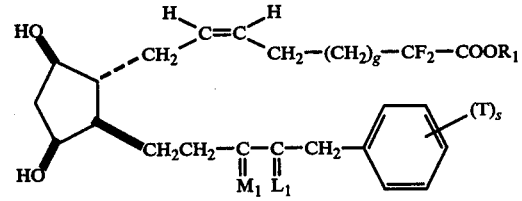
18,19,20-trinor-2,2-difluoro-13,14-dihydro-11β-PGF$_{2\beta}$-type compounds

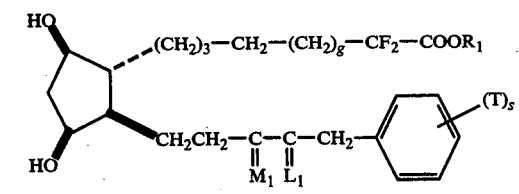
18,19,20-trinor-2,2-difluoro-13,14-dihydro-11β-PGF$_{1\beta}$-type compounds

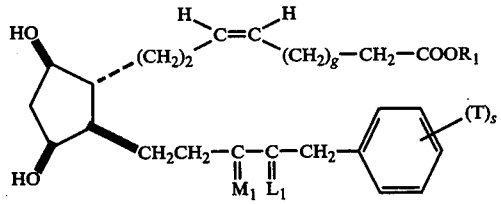
18,19,20-trinor-cis-4,5-didehydro-11β-PGF$_{1\beta}$-type compounds

Table B-continued

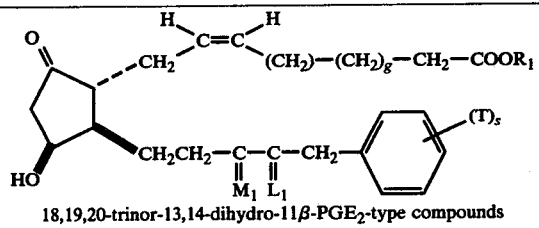
18,19,20-trinor-13,14-dihydro-11β-PGE$_2$-type compounds

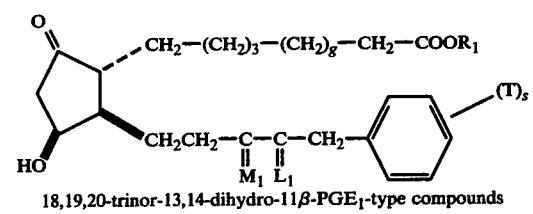
18,19,20-trinor-13,14-dihydro-11β-PGE$_1$-type compounds

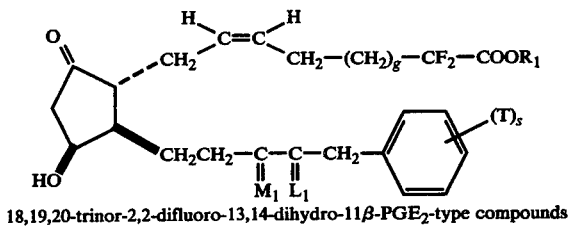
18,19,20-trinor-2,2-difluoro-13,14-dihydro-11β-PGE$_2$-type compounds

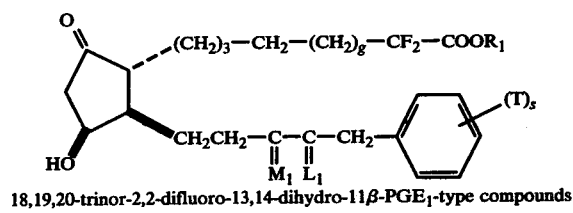
18,19,20-trinor-2,2-difluoro-13,14-dihydro-11β-PGE$_1$-type compounds

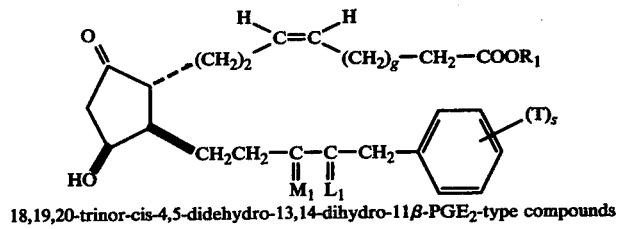
18,19,20-trinor-cis-4,5-didehydro-13,14-dihydro-11β-PGE$_2$-type compounds

| Example | g | s | T | $L_1$ $R_3$ | $R_4$ | $M_1$ $R_5$ | ~OH | $R_1$ | Name |
|---|---|---|---|---|---|---|---|---|---|
| B-1 | 1 | 0 |  | hydrogen | hydrogen | hydrogen | α | hydrogen | 17-phenyl |
| B-2 | 1 | 1 | p-fluoro | hydrogen | hydrogen | hydrogen | α | hydrogen | 17-(p-fluorophenyl) |
| B-3 | 1 | 1 | m-chloro | hydrogen | hydrogen | hydrogen | α | hydrogen | 17-(m-chlorophenyl) |
| B-4 | 1 | 1 | m-tri-fluoromethyl | hydrogen | hydrogen | hydrogen | α | hydrogen | 17-(m-trifluoromethylphenyl) |
| B-5 | 1 | 0 |  | hydrogen | hydrogen | methyl | α | hydrogen | 15-methyl-17-phenyl |
| B-6 | 1 | 1 | p-fluoro | hydrogen | hydrogen | methyl | α | hydrogen | 15-methyl-17-(p-fluorophenyl) |
| B-7 | 1 | 1 | m-chloro | hydrogen | hydrogen | methyl | α | hydrogen | 15-methyl-17-(m-chlorophenyl) |
| B-8 | 1 | 1 | m-tri-fluoromethyl | hydrogen | hydrogen | methyl | α | hydrogen | 15-methyl-17-(m-trifluoromethylphenyl) |
| B-9 | 1 | 0 |  | methyl | methyl | hydrogen | α | hydrogen | 16,16-dimethyl-17-phenyl |
| B-10 | 1 | 1 | p-fluoro | methyl | methyl | hydrogen | α | hydrogen | 16,16-dimethyl-17-(p-fluorophenyl) |
| B-11 | 1 | 1 | m-chloro | methyl | methyl | hydrogen | α | hydrogen | 16,16-dimethyl-17-(m-chlorophenyl) |
| B-12 | 1 | 1 | m-tri-fluoromethyl | methyl | methyl | hydrogen | α | hydrogen | 16,16-dimethyl-17-(m-trifluoromethylphenyl) |
| B-13 | 1 | 0 |  | methyl | methyl | methyl | α | hydrogen | 15,16,16-trimethyl-17-phenyl |
| B-14 | 1 | 1 | p-fluoro | methyl | methyl | methyl | α | hydrogen | 15,16,16-trimethyl-17-(p-fluorophenyl) |
| B-15 | 1 | 1 | m-chloro | methyl | methyl | methyl | α | hydrogen | 15,16,16-trimethyl-17-(m-chlorophenyl) |
| B-16 | 1 | 1 | m-tri-fluoromethyl | methyl | methyl | methyl | α | hydrogen | 15,16,16-trimethyl-17-(m-trifluoromethylphenyl) |
| B-17 | 3 | 0 |  | hydrogen | hydrogen | hydrogen | α | hydrogen | 2a,2b-dihomo-17-phenyl |
| B-18 | 3 | 1 | p-fluoro | hydrogen | hydrogen | hydrogen | α | hydrogen | 2a,2b-dihomo-17-(p-fluorophenyl) |

Table B-continued

| | | | | | | | | | |
|---|---|---|---|---|---|---|---|---|---|
| B-19 | 3 | 1 | m-chloro | hydrogen | hydrogen | hydrogen | α | hydrogen | 2a,2b-dihomo-17-(m-chlorophenyl) |
| B-20 | 3 | 1 | m-trifluoro | hydrogen | hydrogen | hydrogen | α | hydrogen | 2a,2b-dihomo-17-(m-trifluorophenyl) |
| B-21 | 3 | 0 | | hydrogen | hydrogen | methyl | α | hydrogen | 2a,2b-dihomo-15-methyl-17-phenyl |
| B-22 | 3 | 1 | p-fluoro | hydrogen | hydrogen | methyl | α | hydrogen | 2a,2b-dihomo-15-methyl-17-(p-fluorophenyl) |
| B-23 | 3 | 1 | m-chloro | hydrogen | hydrogen | methyl | α | hydrogen | 2a,2b-dihomo-15-methyl-17-(m-chlorophenyl) |
| B-24 | 3 | 1 | m-trifluoromethyl | hydrogen | hydrogen | methyl | α | hydrogen | 2a,2b-dihomo-15-methyl-17-(m-trifluoromethylphenyl) |
| B-25 | 1 | 0 | | fluoro | fluoro | hydrogen | α | hydrogen | 16,16-difluoro-17-phenyl |
| B-26 | 1 | 1 | p-fluoro | fluoro | fluoro | hydrogen | α | hydrogen | 16,16-difluoro-17-(p-fluorophenyl) |
| B-27 | 1 | 1 | m-chloro | fluoro | fluoro | hydrogen | α | hydrogen | 16,16-difluoro-17-(m-chlorophenyl) |
| B-28 | 1 | 1 | m-trifluoromethyl | fluoro | fluoro | hydrogen | α | hydrogen | 16,16-difluoro-17-(m-trifluoromethylphenyl) |
| B-29 | 1 | 0 | | fluoro | fluoro | methyl | α | hydrogen | 15-methyl-16,16-difluoro-17-phenyl |
| B-30 | 1 | 1 | p-fluoro | fluoro | fluoro | methyl | α | hydrogen | 15-methyl-16,16-difluoro-17-(p-fluorophenyl) |
| B-31 | 1 | 1 | m-chloro | fluoro | fluoro | methyl | α | hydrogen | 15-methyl-16,16-difluoro-17-(m-chlorophenyl) |
| B-32 | 1 | 1 | m-trifluoromethyl | fluoro | fluoro | methyl | α | hydrogen | 15-methyl-16,16-difluoro-17-(m-trifluoromethylphenyl) |

I claim:

1. A prostaglandin analog of the formula

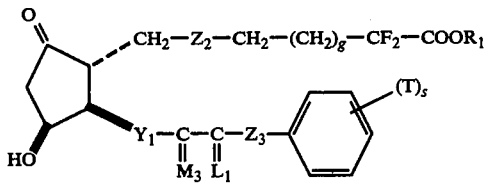

wherein $L_1$ is

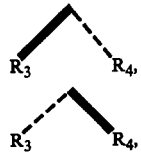

or a mixture of

and

wherein $R_3$ and $R_4$ are hydrogen or methyl, being the same or different;
wherein $M_3$ is

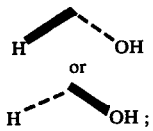

wherein T is chloro, fluoro, trifluoromethyl, alkyl of 1 to 3 carbon atoms, inclusive, or alkoxy of 1 to 3 carbon atoms, inclusive, and s is 0, one, 2, or 3, the various T's being the same or different, with the proviso that not more than two T's are other than alkyl;
wherein $Y_1$ is trans-CH=CH— or —CH$_2$CH$_2$—;
wherein $Z_2$ is
 (1) cis-CH=CH, or
 (2) —(CH$_2$)$_2$—;
wherein g is 1, 2, or 3; and
wherein $R_1$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of 1 to 3 carbon atoms, inclusive, or a pharmacologically acceptable cation.

2. A compound according to claim 1, wherein s is 0 or 1 and T is chloro, fluoro, or trifluoromethyl.

3. A compound according to claim 2, wherein $Z_2$ is —(CH$_2$)$_2$—.

4. A compound according to claim 2, wherein $Z_2$ is cis-CH=CH—.

5. A compound according to claim 4, wherein $Y_1$ is —CH$_2$CH$_2$—.

6. A compound according to claim 4, wherein $Y_1$ is trans-CH=CH—.

7. A compound according to claim 6, wherein $M_1$ is

8. A compound according to claim 7, wherein $M_1$ is

9. A compound according to claim 8, wherein g is 1.

10. A compound according to claim 9, wherein at least one of $R_3$ and $R_4$ is methyl.

11. A compound according to claim 10, wherein $R_3$ and $R_4$ are both methyl.

12. 2,2-Difluoro-16-methyl-16-phenoxy-18,19,20-trinor-11β-PGE$_2$, methyl ester, a compound according to claim 11.

13. A compound according to claim 9, wherein $R_3$ and $R_4$ are both hydrogen.

14. 2,2-Difluoro-16-phenoxy-17,18,19,20-tetranor-11β-PGE$_2$, methyl ester, a compound according to claim 13.

15. A prostaglandin analog of the formula

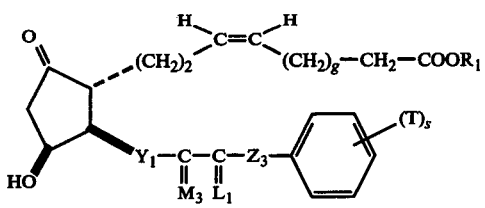

wherein L$_1$ is

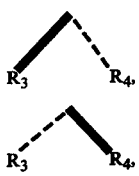

or a mixture of

-continued
and

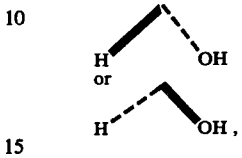

wherein R$_3$ and R$_4$ are hydrogen or methyl, being the same or different;
wherein M$_3$ is H̄ ⟋⟍ OH
or
H̄ ⟋⟍ OH, wherein T is chloro, fluoro, trifluoromethyl, alkyl of 1 to 3 carbon atoms, inclusive, or alkoxy of 1 to 3 carbon atoms, inclusive, and s is 0, 1, 2, or 3, the various T's being the same or different, with the proviso that not more than two T's are other than alkyl;
wherein Y$_1$ is trans-CH=CH— or —CH$_2$CH$_2$—;
wherein g is 1, 2, or 3; and
wherein R$_1$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of 1 to 3 carbon atoms, inclusive, or a pharmacologically acceptable cation.

* * * * *

UNITED STATES PATENT AND TRADEMARK OFFICE
CERTIFICATE OF CORRECTION

PATENT NO. : 4,128,725

DATED : December 5, 1978

INVENTOR(S) : Ernest W. Yankee

It is certified that error appears in the above—identified patent and that said Letters Patent is hereby corrected as shown below:

Column 5, line 46, "reproductive organis" should read -- reproductive organs --;

Column 13, line 62, "-$CH_2$-O-$CH_2$($CH_2$)g-$CH_2$-" should read -- -$CH_2$-O-$CH_2$-($CH_2$)g-$CH_2$- --;

Column 25, line 2, "formula XXXIII" should read -- formula XXXII --;

Columns 45-46, that part of the third formula reading

" 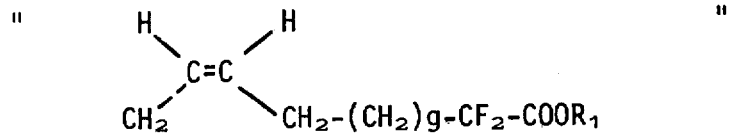 "

should read

-- 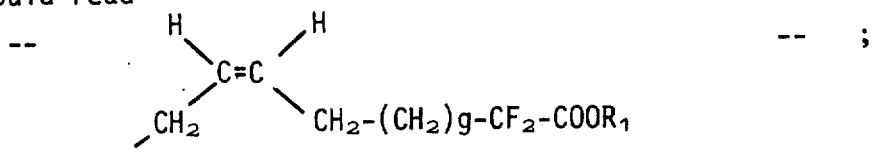 --;

Columns 45-46, that part of the fourth formula reading

"
H       H
 \\   //
  C=C
 /    \\
$CH_2$    $CH_2$-($CH_2$)g-$CF_2$-$COOR_1$
"

should read

--
H       H
 \\   //
  C=C
 /    \\
$CH_2$    $CH_2$-($CH_2$)g-$CF_2$-$COOR_1$
-- ;

UNITED STATES PATENT AND TRADEMARK OFFICE
CERTIFICATE OF CORRECTION

PATENT NO. : 4,128,725
DATED : December 5, 1978
INVENTOR(S) : Ernest W. Yankee

It is certified that error appears in the above—identified patent and that said Letters Patent is hereby corrected as shown below:

Columns 45-46, that part of the last formula reading

" \\(CH$_2$)-(CH$_2$)g-CM$_2$-COOR$_1$ "

should read

-- \\CH$_2$-(CH$_2$)g-CH$_2$-COOR$_1$ -- .

Signed and Sealed this

Twenty-ninth Day of September 1981

[SEAL]

Attest:

Attesting Officer

GERALD J. MOSSINGHOFF

Commissioner of Patents and Trademarks